United States Patent
Singh et al.

(10) Patent No.: US 9,816,227 B2
(45) Date of Patent: Nov. 14, 2017

(54) TEXTILE PRODUCTS WITH HERBAL COMPOSITION TO RENDER THE FABRICS INSECTS REPELLENT

(71) Applicant: SYNTIS TEXTILE PRIVATE LIMITED, Mumbai (IN)

(72) Inventors: Kamal Nayan Singh, Ghaziabad (IN); Mukund Rangrao Galgali, Thane (IN)

( * ) Notice: Subject to any disclaimer, the term of this patent is extended or adjusted under 35 U.S.C. 154(b) by 15 days.

(21) Appl. No.: 14/778,699

(22) PCT Filed: May 3, 2013

(86) PCT No.: PCT/IN2013/000295
§ 371 (c)(1),
(2) Date: Oct. 6, 2015

(87) PCT Pub. No.: WO2014/147632
PCT Pub. Date: Sep. 25, 2014

(65) Prior Publication Data
US 2016/0047086 A1   Feb. 18, 2016

(30) Foreign Application Priority Data
Mar. 21, 2013  (IN) ............................ 971/MUM/2013

(51) Int. Cl.
*D06P 3/00* (2006.01)
*D06M 16/00* (2006.01)
*D06M 13/352* (2006.01)
*D06P 1/00* (2006.01)
*A01N 65/26* (2009.01)
(Continued)

(52) U.S. Cl.
CPC ............. *D06M 16/00* (2013.01); *A01N 43/12* (2013.01); *A01N 43/90* (2013.01); *A01N 45/00* (2013.01); *A01N 65/26* (2013.01); *D06M 13/148* (2013.01); *D06M 13/224* (2013.01);
(Continued)

(58) Field of Classification Search
CPC ........ A01N 65/26; A01N 45/00; A01N 43/12; A01N 25/10; A01N 25/34; D06M 3/148; D06M 13/228; D06M 16/00; D06M 13/232; D06M 13/224; D06P 1/0036
See application file for complete search history.

(56) References Cited

U.S. PATENT DOCUMENTS 5,885,600 A * 3/1999 Blum ................. A01N 65/00
424/405
2010/0069811 A1   3/2010 Poddar
2012/0309077 A1  12/2012 Sachdev

* cited by examiner

*Primary Examiner* — Eisa Elhilo
(74) *Attorney, Agent, or Firm* — Barry Choobin; Patent 360

(57) ABSTRACT

The present invention provides a herbal composition for treating a fabric to make the fabric insect repellent. The present invention further provides a composition for treating a fabric and a method of treating the fabric to make the fabric insect repellent. The invention also provides the various methods of treating different kinds of fabrics along with their dyeing and finishing processes to render the fabric insect repellant. The fabric becomes insect repellant up to 40 washes. The fabric becomes repellent against bed bugs of *Cimex* species, house dust mites of *Dermatophagoides* species, ticks of *Ixodes* species, houseflies or *Musca Domestica*, mosquitoes or *Aedes Aegypti* and harvest bugs of *Trombidium* species. The fabric is selected from the group consisting of a cotton fabric, a regenerated viscose cellulose fabric, a wool fabric, a silk fabric, a polyester fabric and blends thereof.

17 Claims, 8 Drawing Sheets

(51) Int. Cl.
*D06M 13/224* (2006.01)
*A01N 43/12* (2006.01)
*A01N 43/90* (2006.01)
*A01N 45/00* (2006.01)
*D06M 13/148* (2006.01)
*D06M 13/228* (2006.01)
*D06M 13/232* (2006.01)

(52) U.S. Cl.
CPC ........ *D06M 13/228* (2013.01); *D06M 13/232* (2013.01); *D06M 13/352* (2013.01); *D06P 1/0036* (2013.01)

TEXTILE PRODUCTS WITH HERBAL COMPOSITION TO RENDER THE FABRICS INSECTS REPELLENT

PRIORITY DATA

This non-provisional application is filed claiming priority from an Indian patent application filed on 21 Mar. 2013 with application no. 971/MUM/2013.

BACKGROUND

Technical Field of Invention

The embodiments of the present invention generally relate to a novel herbal composition and the use of the novel herbal composition for treating the textile fabrics. The embodiments more particularly relate to a Neem tree based herbal composition used for treating fabrics to render them insect repellent.

Description of Related Art

The human household and surroundings have been a favorable dwelling place for a plenty of pests. The pests live and grow along with the humans and sometimes harm the humans. Such pests have been specified as being parasites. The parasites invade the humans and their surroundings and adversely affect their quality of life. The parasites are categorized as endo-parasites and exo-parasites depending upon their place of growth and mode of inflicting harm to the humans. The endo-parasites are the organisms that grow and live inside the human's body and damage the internal organs by drawing nutrition through them. The exo-parasites on the contrary are the organisms that grow and live outside the human body in their surroundings. The exo-parasites include bed bugs, house dust mites, houseflies, mosquitoes, harvest bugs and many other arthropods. The exo-parasites harm the humans in many ways such as these parasites feed on human blood or cause health problems due to allergy, etc.

The textiles have always been the most intimate belonging of humans. Such textiles include the apparels that are worn by the humans and the home textiles which are being used by the humans for their daily scores of living. The textiles in this manner have remained closest to the humans among the other surroundings. The parasites under discussion have found very easy approach to the textiles and the textile products being used by the humans. Therefore, textiles remain the most susceptible medium where the problem starts and grows causing inconvenience and harm to the humans.

There have been methods that help in eradicating the growth of these parasites. There have been solutions which are in the form of pesticide sprays. The sprayed material is mixed in the atmosphere and settles down on all of the objects in the human surroundings and repels or kills the exo-parasites when in contact. The pesticide sprays make the exo-parasites leave human surroundings. The effectiveness of the sprayed material remains till it is not diminished.

The problem of exo-parasite infestation in the human surroundings has been widespread globally since a longer time. Many more initiatives have been taken in the past to ward off this problem however its menace is increasing the intensity keeping in view the increasing human population, complicated human lifestyle and increasing immunity of the parasites against the eradication measures in use.

There have been some solutions where chemicals of inorganic origin are incorporated into textile processing for creating the desired effects. These chemicals are pesticides and may not be safe for humans and may cause damage to the ecosystem too in a long run.

Other solutions to this problem are in the form of materials that are used as coils or liquid vaporizers. The coils or liquid vaporizers slowly but continuously emit the chemical fumes or vapors. The fumes or vapors are harmful to the exo-parasites like mosquitoes, houseflies, etc. and repel them out of the human surroundings.

There have been electronic gadgets which emit ultrasonic waves that are unbearable to the exo-parasites. The ultrasonic waves are not audible to the humans but repel the parasites out of the human surroundings.

Mechanical devices combined with chemicals fitted onto the textile materials like mattresses, etc. that detect, attract, aggregate, arrest pests like bed bugs and eradicate them.

But the available prior arts have various drawbacks such as less effectiveness, limitations of application on textiles and toxicity to the humans and the environment. To have more effective solution to the problem, it is very much required that the treatment done should be long lived. Otherwise the effect remains temporary and the parasites that might have been repelled by the solution or treatment may come back and infest the human surroundings thus defeating the purpose of the solution grossly. In case of pesticide spray mechanism for repelling the parasites, the spray mist is mixed into the atmosphere and the particles settle down on the objects in the human surroundings. This effect is short lived and the parasite grows again and starts dwelling in the human surroundings once the pesticide's concentration in the atmosphere or objects is diminished.

Similarly in case of repellent chemicals being used in the form of coil or liquid vapor also have a very short life and hence effectiveness of the solution remains underrated for human purposes. In case of solution where electronic gadgets are used that emit ultrasonic waves for the repelling parasites, the effectiveness is good or satisfactory initially, but at later point of time the parasites develop immunity and become sustainable against the effectiveness of the solution. Thus the longevity of the effectiveness of these solutions also comes under doubts.

Also the spray mechanism cannot be applied on all kinds of textile products because the chemicals or pesticides are not human skin friendly. Further, the use of materials in the form of the coils or liquid vapor and the electronic gadgets which emit ultrasonic waves does not have any applicability on the textile products. The currently available products are not that safe for the human usages and cause ecological disturbances in the long terms. The pesticides that are sprayed into the human surroundings are absolutely not safe for humans and other organism because the said pesticides comprise chemicals that cause health hazards and poses long term major environmental pollution by integrating themselves into the environmental resources and travelling down the ecological pyramid. Similarly, the chemicals that are used in the form of coils or liquids emit the fumes or vapors that are not safe to humans and pose environmental threats in the long run.

The electronic gadgets emitting ultrasonic waves may not be polluting the environment but may pose health hazard to the humans as well as to the other organisms in a long run by affecting the internal organs or the nervous system but still may remain unnoticed of creating such damages so.

Hence there is a need to provide a composition that is capable of eradicating the growth of the exo-parasites in the textiles used by the humans. Also there is a need to provide an eco-friendly, easy to apply and cost effective method of treating such textiles with a processing composition to make the fabrics insect repellent.

The above mentioned shortcomings, disadvantages and problems are addressed herein, as detailed below.

SUMMARY OF THE INVENTION

The primary object of the present invention is to provide a herbal composition to eradicate the growth of insects in the textiles or fabrics.

Another object of the present invention is to provide a Neem based herbal composition that is eco-friendly and poses less harm to the humans and the environment.

Yet another object of the present invention is to provide a method of treating a plurality of fabrics with a plurality of finishes to render them insect repellant.

Yet another object of the present invention is to provide a method that is eco-friendly, economic and easy to apply on the fabrics.

Yet another object of the present invention is to provide a composition and a method of treating a fabric to render them repellent towards a wide range of arthropods.

Yet another object of the present invention is to provide a composition and a method of treating a fabric to provide a long lasting insect repellant property that distracts and repels parasites like bed bugs, house dust mites, ticks, houseflies, mosquitoes and many other pests so that the humans are not attacked by them while using such treated textile products.

The various embodiments of the present invention provide a herbal composition for rendering the fabrics insect repellant. The embodiments herein also provide a method of treating a fabric with the herbal composition to make the fabric insect repellant. The embodiments also provide various methods of treating the fabric during the various stages of dyeing and finishing processes.

In an embodiment, a composition for treating a fabric to make the fabric insect repellent is provided. The composition comprises a herbal formulation, a pigment binder, an anti-thermo migrating agent, an amino silicon emulsion, a Glauber's salt and an acetic acid. The herbal composition comprises Bioflavonoids. The bioflavoboids are Azadirachtin, Azadiradione, Fraxinellone, Nimbin, Salannin, Salannol, Vepinin and Vilasinin. The pigment binder is poly acrylate binder. The anti-thermo migrating agent is a humectant. The amino silicon emulsion is a permanent softener.

In another embodiment, the composition comprises of a herbal formulation and a plurality of processing auxiliaries. The herbal composition comprises Bioflavonoids. The bioflavoboids are Azadirachtin, Azadiradione, Fraxinellone, Nimbin, Salannin, Salannol, Vepinin and Vilasinin. The plurality of processing auxiliaries comprises a pigment binder, an anti-thermo migrating agent, an amino silicon emulsion, a Glauber's salt and an acetic acid. The pigment binder is poly acrylate binder. The anti-thermo migrating agent is a humectant. The amino silicon emulsion is a permanent softener. The processing of the fabric is done with the help of the plurality of processing auxiliaries.

The azadiradione is present in an amount of 30 to 250 ppm. The fraxinellone is present in an amount of 15 to 125 ppm. The nimbin is present in an amount of 450 to 2400 ppm. The salannin is present in an amount of 110 to 2050 ppm. The salannol is present in an amount of 168 to 3800 ppm. The vepinin is present in an amount of 15 to 125 ppm and the vilasinin is present in an amount of 15 to 125 ppm.

The pigment binder is present in an amount of 12-15 gpl. The anti-thermo migrating agent is present in an amount of 2-5 gpl. The amino silicon emulsion is present in an amount of 5 gpl. The Glauber's salt is present in an amount of 5 gpl and the acetic acid is present in an amount of 0.5 gpl.

In another embodiment, a method of treating a fabric to make the fabric insect repellent is provided. The method comprises adding an herbal composition along with a plurality of additives in a fabric process at a predetermined temperature and at a pre-determined pH. The herbal composition comprises azadirachtin, azadiradione, fraxinellone, nimbin, salannin, salannol, vepinin and vilasinin. The plurality of additives includes a pigment binder, an anti-thermo migrating agent, an amino silicon emulsion, a Glauber's salt and an acetic acid. The fabric process is a process selected from the group consisting of a sanforization process, a bleach finishing process, a dyed finishing process, and a two step dyeing method for cotton or polyester blended fabric. The dyed finishing process further comprises a dyeing on jigger using a Vat dye, dyeing on jigger using a reactive dye, dyeing by a pad batch method using reactive dyes, dyeing by pad cure method using reactive dyes, continuous dyeing on a Continuous Dyeing Range Machine (CDR) or a Stenter machine with a pigment ink of any class of dyes. The predetermined temperature is in a range of 60° C.-160° C. and the predetermined pH is in a range of 5.5-6.5. The herbal composition is added in an amount of 20-25 gpl. The fabric becomes repellent to a plurality of insects after the treatment. The plurality of insects are bed bugs of *Cimex* species, house dust mites of *Dermatophagoides* species, ticks of *Ixodes* species, houseflies or *Musca Domestica*, mosquitoes or *Aedes Aegypti* and harvest bugs of *Trombidium* species. The fabric is selected from the group consisting of a cotton fabric, a regenerated viscose cellulose fabric, a wool fabric, a silk fabric, a polyester fabric and blends thereof. The fabric is insect repellent up to 40 times of washes.

In another embodiment, a method of treating a bleached fabric to render the bleached fabric insect repellent is provided. The method comprises preparing a herbal composition. The herbal composition is prepared by adding a predetermined amount of azadiradione, a predetermined amount of fraxinellone, a predetermined amount of nimbin, a predetermined amount of salannin, a predetermined amount of salannol, a predetermined amount of vepinin and a predetermined amount of vilasinin. The predetermined amount of azadiradione added is 30 to 250 ppm, the predetermined amount of fraxinellone added is 15 to 125 ppm, the predetermined amount of nimbin added is 450 to 2400 ppm, the predetermined amount of salannin added is 110 to 2050 ppm, the predetermined amount of salannol added is 168 to 3800 ppm, the predetermined amount of vepinin added is 15 to 125 ppm and the predetermined amount of vilasinin added is 15 to 125 ppm. The herbal composition is taken in an amount of 20-25 gpl in a treatment machine. A predetermined amount of a plurality of additives is added to the treatment machine. The plurality of additives are a pigment binder, an anti-thermo migrating agent, an amino silicon emulsion, a Glauber's salt and an acetic acid. The predetermined amount of the pigment binder is 12-15 gpl, the predetermined amount of the anti-thermo migrating agent is 2-5 gpl, the predetermined amount of the amino silicon emulsion is 5 gpl, the predetermined amount of the Glauber's salt is 5 gpl, and the predetermined amount of the acetic acid is 0.5 gpl. The fabric is padded, dried and cured simultaneously at 160° C. at a speed of 22 to 25 meters/min and sanforized.

In another embodiment, a method of treating a fabric on a Stenter machine to render the fabric insect repellent is provided. The method comprises taking a fabric of any count and construction along with a blend composition. The fabric padded a Stenter machine using a solution of a herbal composition. The herbal composition comprises an azadiradione in an amount of 30 to 250 ppm, a fraxinellone in an amount of 15 to 125 ppm, a nimbin in an amount of 450 to 2400 ppm, a salannin in amount of 110 to 2050 ppm, a salannol in an amount of 168 to 3800 ppm, a vepinin in amount of 15 to 125 ppm and a vilasinin in an amount of 15 to 125 ppm. The herbal composition is used in an amount of 22-25 gpl. A plurality of additives is added in the Stenter machine. The plurality of additives includes a pigment binder in an amount of 12-15 gpl, a anti-thermo migrating agent in an amount of 2-5 gpl, a amino silicon emulsion in an amount of 5 gpl, a Glauber's salt in an amount of 5 gpl and an acetic acid in an amount of 0.5 gpl. The fabric is dried on the Stenter machine while maintaining a temperature from 110° C. in a first compartment followed by 160° C. in next two compartments of the Stenter machine at a speed of 20-25 Mtrs of fabric per minute in the Stenter machine. The fabric is batched on a roll after the drying. The fabric is folded and packaged. The fabric is selected from the group consisting of a bleached fabric, a VAT dyed fabric, a reactive dyed fabrics, a pigment ink dyed fabric and a combination thereof.

In another embodiment, a method of treating a fabric while dyeing and finishing on a Continuous Dyeing Range (CDR) machine or on a Stenter machine using a pigment ink of any class of dyes to render the fabric insect repellent is provided. The method comprises taking a fabric of any count and construction along with a blend composition. The fabric is padded on a machine using a solution of a herbal composition, solution of plurality of additives and a solution of a pigment ink. The herbal composition comprises an azadiradione in an amount of 30 to 250 ppm, a fraxinellone in an amount of 15 to 125 ppm, a nimbin in an amount of 450 to 2400 ppm, a salannin in amount of 110 to 2050 ppm, a salannol in an amount of 168 to 3800 ppm, a vepinin in amount of 15 to 125 ppm and a vilasinin in an amount of 15 to 125 ppm, and the herbal composition is used in an amount of 22-25 gpl. The plurality of additives includes a pigment binder in an amount of 12-15 gpl, an anti-thermo migrating agent in an amount of 2-5 gpl, an amino silicon emulsion in an amount of 5 gpl, a Glauber's salt in an amount of 5 gpl and an acetic acid in an amount of 0.5 gpl, and the solution of a pigment ink is used in an amount of upto 5 gpl. The machine is selected from the group consisting of a CDR machine and a Stenter machine. The fabric is dried on the machine while maintaining a temperature from 110° C.-160° C. at a speed. The speed in a Stenter machine is at 20-25 Mtrs of fabric per minute. The speed in a CDR machine is 40-60 Mtrs of fabric per Minute. The fabric is batched on roll after the drying. The fabric is then folded and packaged.

In another embodiment, a method of treating a fabric while dyeing and finishing on a Jigger machine using a dye to render the fabric insect repellent is provided. The method comprises taking a fabric and loading the fabric on a Jigger machine along with a cold water. A dye solution is added in the cold water while undergoing at least two cycles for 1 hour in the Jigger machine. The temperature of the Jigger machine is raised up to 60° C. while again undergoing at least two cycles for 1 hour in the Jigger machine. A pre-determined quantity of Glauber's salt is added to the cold water while again undergoing at least two cycles for 1 hour in the Jigger machine. The pre-determined quantity of Glauber's salt is 10-20 gpl. A pre-determined quantity of a caustic soda (NaOH), a pre-determined quantity of a Sodium Hydro Sulphite (Na2S2O4) and a pre-determined quantity of the herbal composition is added while again undergoing at least two cycles for 1 hour in the Jigger machine. The pre-determined quantity of the caustic soda (NaOH) is 10 gpl, the pre-determined quantity of the Sodium Hydro Sulphite (Na2S2O4) is 10 gpl and the pre-determined quantity of the herbal composition is 4% w/w. The bath liquor is drained out from the Jigger machine. Fresh water is added in the Jigger machine. A pre-determined quantity of Hydrogen Peroxide (H2O2) of 50% strength is added into the bath in the Jigger machine. The pre-determined quantity of Hydrogen Peroxide is 0.50 gpl. The temperature of the bath is raised up to 60° C. The fabric is washed with a detergent inside the Jigger machine. The fabric is unloaded from the Jigger machine and dried on drying cylinders. The dye is selected from the group consisting of a VAT dye and a Reactive dye.

In another embodiment, a method of treating a fabric in a Pad Batch Method of dyeing to render the fabric insect repellent is provided. The method comprises taking a fabric and passing the fabric in a padding mangle machine having a mixture. The mixture comprises Sodium Silicate (Na2SiO3), a dye and a herbal composition. The quantity of the herbal composition is 20-25 gpl. The fabric is padded through the mixture and batched on a roll. A dye is fixed on the fabric roll. The fabric is washed in a Jigger machine by raising the temperature of a bath up to 60° C. and undergoing at least two cycles on the Jigger machine with fresh water. The fabric is unloaded and dried. The herbal composition comprises azadiradione in an amount of 30 to 250 ppm, fraxinellone in an amount of 15 to 125 ppm, nimbin in an amount of 450 to 2400 ppm, salannin in an amount of 110 to 2050 ppm, salannol in an amount of 168 to 3800 ppm, vepinin in an amount of 15 to 125 ppm and vilasinin in an amount of 15 to 125 ppm.

In another embodiment, a method of treating a fabric in a Pad Cure Method of dyeing to render the fabric insect repellent is provided. The method comprises taking a fabric and passing the fabric in a padding mangle machine having a mixture. The mixture comprises 5-10 gpl of a Sodium Bicarbonate (NaHCO3) and 20-25 gpl of a herbal composition. The fabric is padded through the mixture. The fabric is dried in a Dryer and batched. The fabric is then cured in a curing chamber for at least 5 minutes at a temperature of 160° C. while maintaining a speed at 40-50 Mtrs of fabric per minute. The cured fabric is then loaded in a Jigger machine. The fabric is washed with a detergent in the Jigger machine while raising the temperature of a bath up to 60° C. and undergoing at least two cycles on the Jigger machine. The fabric is washed with fresh water in the Jigger machine while raising the temperature of the bath up to 60° C. and undergoing at least two cycles on the Jigger machine. The fabric is then washed with a cold water while undergoing at least two cycles on the Jigger machine. The fabric is collected and dried on the drying cylinders. The herbal composition comprises azadiradione in an amount of 30 to 250 ppm, fraxinellone in an amount of 15 to 125 ppm, nimbin in an amount of 450 to 2400 ppm, salannin in an amount of 110 to 2050 ppm, salannol in an amount of 168 to 3800 ppm, vepinin in an amount of 15 to 125 ppm and vilasinin in an amount of 15 to 125 ppm.

In another embodiment, a method of treating a polyester fabric to render the fabric insect repellent is provided. The method comprises taking the fabric and loading the fabric in a JET Dyeing Machine along with water. A pre-determined amount of an acetic acid is added to the machine to maintain a pre-determined pH. The pre-determined amount of the acetic acid is 0.50 gpl and the pre-determined pH is 4.5 to 5.5. The fabric is circulated along with the water in the Jet Dyeing Machine for at least 10 minutes at a speed of 80 Mtrs per minute. A dye solution is prepared and slowly released in the Jet Dyeing machine and the temperature of the machine is raised upto 130° C. The fabric is circulated along with the water in the Jet Dyeing machine for a time period of 45-60 minutes. The liquid is then drained out of the machine. The fabric is washed with in the Jet Dyeing Machine and unloaded from the Jet Dyeing Machine. The fabric is then loaded in a Jigger machine through cold water. A dye solution is added in the Jigger machine. The temperature of the Jigger machine is raised up to 60° C. while undergoing at least two cycles. A pre-determined quantity of a Glauber's salt (Na2SO4) is added while undergoing at least two turns evenly on the Jigger machine. The pre-determined quantity of the Glauber's salt is 10-20 gpl. Then a pre-determined quantity of a Caustic Soda (NaOH) and a pre-determined quantity of a herbal composition is added while undergoing at least two cycles on the Jigger machine. The pre-determined quantity of the Caustic Soda (NaOH) is 10 gpl. The pre-determined quantity of the herbal composition is 4% w/w. The liquid is then drained out of the Jigger machine. The fabric is washed a detergent in the Jigger machine while raising the temperature of a bath up to 60° C. and undergoing at least two cycles on the Jigger machine. The fabric is then washed with fresh water in the Jigger machine while raising the temperature of the bath up to 60° C. and undergoing at least two cycles on the Jigger machine. The fabric is again washed with a cold water while undergoing at least two cycles on the Jigger machine. The fabric is collected and fried on the drying cylinders. The herbal composition comprises azadiradione in an amount of 30 to 250 ppm, fraxinellone in an amount of 15 to 125 ppm, nimbin in an amount of 450 to 2400 ppm, salannin in an amount of 110 to 2050 ppm, salannol in an amount of 168 to 3800 ppm, vepinin in an amount of 15 to 125 ppm and vilasinin in an amount of 15 to 125 ppm.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

DETAILED DESCRIPTION OF THE DRAWINGS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments of the present invention provide an insect repellant herbal composition. The embodiments also provide a composition for treating a large variety of fabrics to render the fabrics insect repellant. The embodiments further provide a method of treating various kinds of fabrics along with their dyeing and finishing processes by incorporating the herbal composition of the present invention to render the fabrics insect repellent.

The terms "textiles", "textile products" and "fabric or fabrics" are used interchangeably in the following detailed description. The terms "composition" and "formulation" are used interchangeably in the following detailed description. The various machineries mentioned in the detailed description are used interchangeably as following "Jigger" or "jigger machine", "Stenter" or "Stenter machine", "CPB" or "Cold Pad Batch Machine", "CDR" or "Continuous Dyeing Range" or "Continuous Dyeing Range machine".

The abbreviations used in the following detailed description has their full names as:
m/f: Microfine
gpl: Grams Per Liter
m:l: Material to Liquor Ratio The herbal composition is designed for various applications into the textiles and the textile products for achieving the insect repellency. The treatment process makes the textiles or the textile products enough capable of repelling insects like bed bugs, house dust mites, houseflies, mosquitoes, ticks, harvest bugs and many more that do infest the human surroundings and affect them negatively in different ways.

Figure 1:
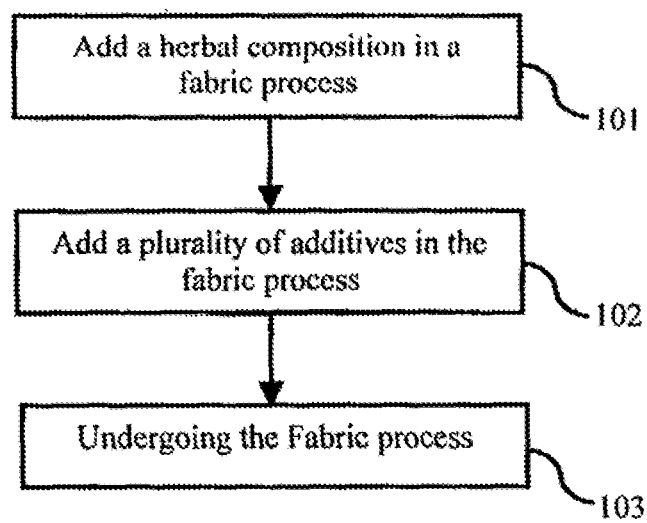
FIG. 1 is a flowchart showing the various steps involved in a method of treating a fabric to make the fabric insect repellent, according to an embodiment herein.

In one embodiment, the method of treatment is carried out in a plurality of fabric dyeing and finishing processes to make the fabric insect repellant. FIG. 1 is a flowchart showing the various steps involved in the method of treating a fabric to make the fabric insect repellant, according to an embodiment herein. With respect to FIG. 1, a pre-determined amount of the herbal composition is added in a fabric process (101). The herbal composition comprises azadiradione, fraxinellone, nimbin, salannin, salannol, vepinin and vilasinin. A plurality of additives is added in the fabric process (102). The plurality of additives includes a pigment binder, an anti-thermo migrating agent, an amino silicon emulsion, a Glauber's salt and an acetic acid. The herbal composition and the plurality of additives are added at a pre-determined temperature and at a pre-determined pH. The predetermined temperature is in a range of 60° C.-160° C. The predetermined pH is in a range of 5.5-6.5. The fabric process is undergone to make the final treated fabric that is insect repellant (103). The fabric process is a process selected from the group consisting of a sanforization process, a bleach finishing process, a dyed finishing process and a two step dyeing method for cotton or polyester blended fabric. The dyed finishing process further comprises a dyeing on jigger using a VAT dye, dyeing on jigger using a reactive dye, dyeing by a pad batch method using reactive dyes, dyeing by pad cure method using reactive dyes, continuous dyeing on a Continuous Dyeing Range Machine (CDR) or a Stenter machine with a pigment ink of any class of dyes. The herbal composition is added in an amount of 20-25 gpl. The fabric becomes repellent to a plurality of insects after the treatment. The plurality of insects are bed bugs of *Cimex* species, house dust mites of *Dermatophagoides* species, ticks of *Ixodes* species, houseflies or *Musca Domestica*, mosquitoes or *Aedes Aegypti* and harvest bugs of *Trombidium* species. The fabric is selected from the group consisting of a cotton fabric, a regenerated viscose cellulose fabric, a wool fabric, a silk fabric, a polyester fabric and blends thereof. The fabric is insect repellent up to 40 times of washes.

Figure 2:
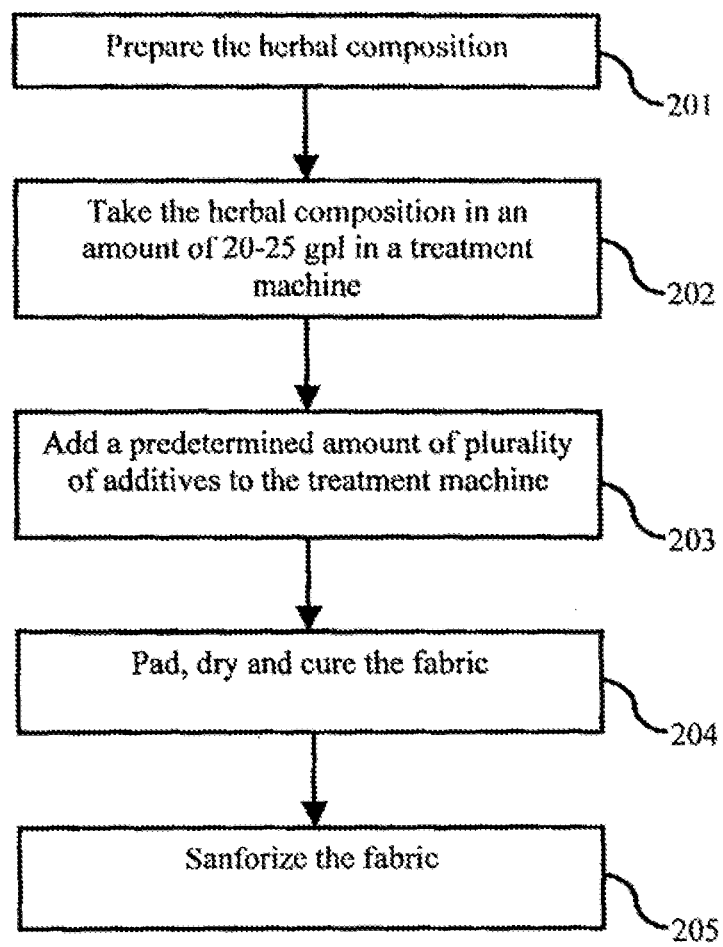
FIG. 2 is a flowchart showing the various steps involved in a method of treating a bleached fabric to render the bleached fabric insect repellent, according to an embodiment herein.

In another embodiment, the method of treating a bleached fabric to render the bleached fabric insect repellent is provided. FIG. 2 is a flowchart showing the various steps involved in the method of treating a bleached fabric to render the bleached fabric insect repellent, according to an embodiment herein. With respect to FIG. 2, an herbal composition is first prepared (201). The herbal composition is prepared by adding a predetermined amount of azadiradione, fraxinellone, nimbin, salannin, salannol, vepinin and vilasinin. The predetermined amount of azadiradione added is 30 to 250 ppm. The predetermined amount of fraxinellone is 15 to 125 ppm. The predetermined amount of nimbin is 450 to 2400 ppm. The predetermined amount of salannin is 110 to 2050 ppm. The predetermined amount of salannol is 168 to 3800 ppm. The predetermined amount of vepinin is 15 to 125 ppm and the predetermined amount of vilasinin is 15 to 125 ppm. The herbal composition is taken in an amount of 20-25 gpl in a treatment machine (202). A predetermined amount of plurality of additives is added to the treatment machine (203). The plurality of additives are a pigment binder, an anti-thermo migrating agent, an amino silicon emulsion, a Glauber's salt and an acetic acid. The predetermined amount of the pigment binder added is 12-15 gpl. The predetermined amount of the anti-thermo migrating agent added is 2-5 gpl. The predetermined amount of the amino silicon emulsion added is 5 gpl. The predetermined amount of the Glauber's salt added is 5 gpl and the predetermined amount of the acetic acid added is 0.5 gpl. The fabric is padded, dried and cured simultaneously at 160° C. at a speed of 22 to 25 meters/min (204). The fabric is taken for sanforization (205).

Figure 3:
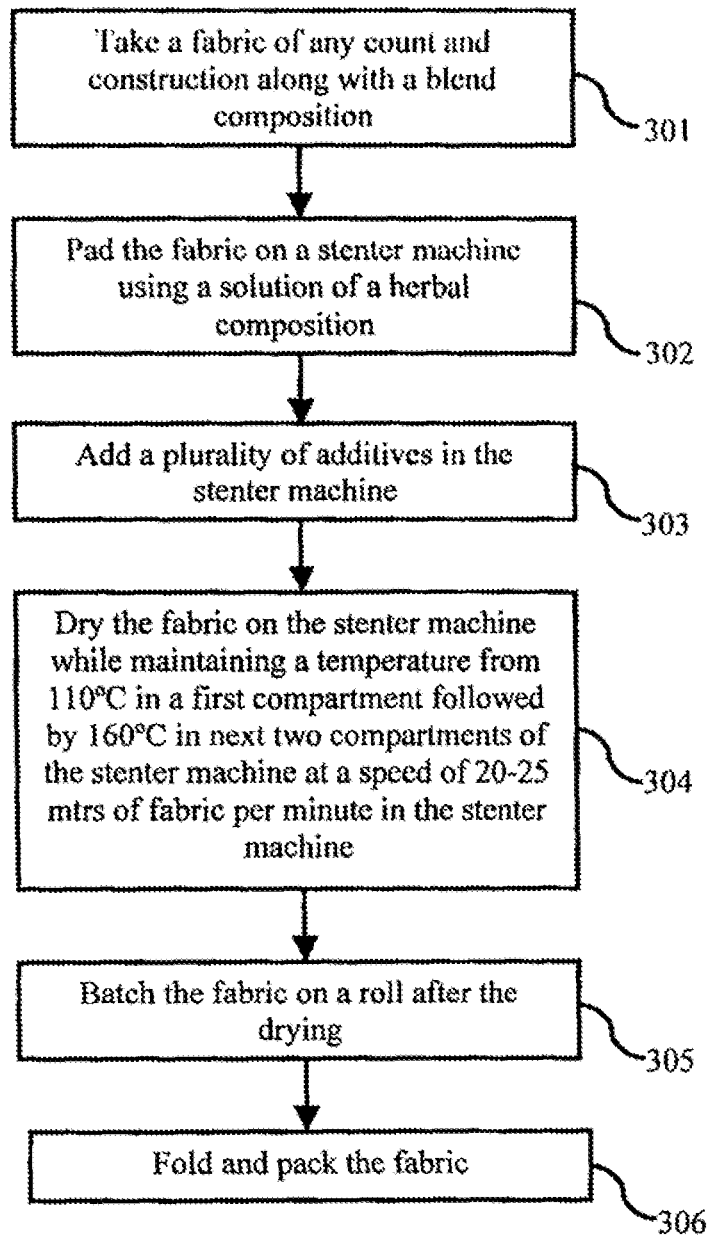
FIG. 3 is a flowchart showing the various steps involved in a method of treating the fabric on a stenter machine to render the fabric insect repellent, according to an embodiment herein.

In another embodiment, the method of treating a fabric on a Stenter machine to render the fabric insect repellent is provided. FIG. 3 is a flowchart showing the various steps involved in the method of treating the fabric on a Stenter machine to render the fabric insect repellent, according to an embodiment herein. With respect to FIG. 3, a fabric of any count and construction along with a blend composition is taken (301). The fabric is padded on a Stenter machine using a solution of a herbal composition (302). The herbal composition comprises an azadiradione in an amount of 30 to 250 ppm, a fraxinellone in an amount of 15 to 125 ppm, a nimbin in an amount of 450 to 2400 ppm, a salannin in amount of 110 to 2050 ppm, a salannol in an amount of 168 to 3800 ppm, a vepinin in amount of 15 to 125 ppm and a vilasinin in an amount of 15 to 125 ppm. The herbal composition is used in an amount of 22-25 gpl. A plurality of additives is added in the Stenter machine (303). The plurality of additives includes a pigment binder in an amount of 12-15 gpl, a anti-thermo migrating agent in an amount of 2-5 gpl, a amino silicon emulsion in an amount of 5 gpl, a Glauber's salt in an amount of 5 gpl and an acetic acid in an amount of 0.5 gpl. The fabric is dried on the Stenter machine while maintaining a temperature from 110° C. in a first compartment followed by 160° C. in next two compartments of the Stenter machine at a speed of 20-25 Mtrs of fabric per minute in the Stenter machine (304). The fabric is batched on a roll after the drying (305). The fabric is folded and packaged (306). The fabric is selected from the group consisting of a bleached fabric, a VAT dyed fabric, a reactive dyed fabrics, and a pigment ink dyed fabric and a combination thereof.

Figure 4:
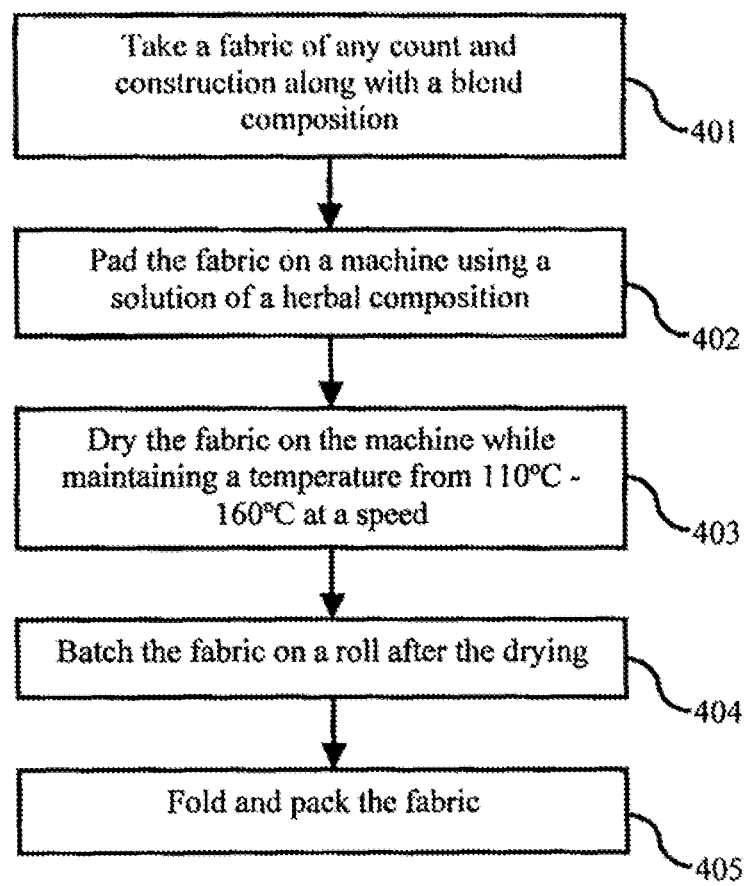
FIG. 4 is a flowchart showing the various steps involved in a method of treating a fabric while dyeing and finishing on a Continuous Dyeing Range (CDR) machine or on a stenter machine using a pigment ink of any class of dyes to render the fabric insect repellent, according to an embodiment herein.

In another embodiment, a method of treating a fabric while dyeing and finishing on a Continuous Dyeing Range (CDR) machine or on a Stenter machine using a pigment ink of any class of dyes to render the fabric insect repellent is provided. FIG. 4 is a flowchart showing the various steps involved in the method of treating a fabric while dyeing and finishing on a Continuous Dyeing Range (CDR) machine or on a Stenter machine using a pigment ink of any class of dyes to render the fabric insect repellent, according to an embodiment herein. With respect to FIG. 4, a fabric of any count and construction along with a blend composition is taken (401). The fabric is padded on a machine using a solution of an herbal composition, the solution of plurality of additives and a solution of a pigment ink (402). The herbal composition comprises an azadiradione in an amount of 30 to 250 ppm, a fraxinellone in an amount of 15 to 125 ppm, a nimbin in an amount of 450 to 2400 ppm, a salannin in amount of 110 to 2050 ppm, a salannol in an amount of 168 to 3800 ppm, a vepinin in amount of 15 to 125 ppm and a vilasinin in an amount of 15 to 125 ppm. The herbal composition is used in an amount of 22-25 gpl. The plurality of additives includes a pigment binder in an amount of 12-15 gpl, an anti-thermo migrating agent in an amount of 2-5 gpl, an amino silicon emulsion in an amount of 5 gpl, a Glauber's salt in an amount of 5 gpl and an acetic acid in an amount of 0.5 gpl. The solution of a pigment ink is used in an amount of upto 5 gpl. The machine is selected from the group consisting of a CDR machine and a Stenter machine. The fabric is dried on the machine while maintaining a temperature from 110° C.-160° C. at a speed (403). The speed in a Stenter machine is at 20-25 Mtrs of fabric per minute. The speed in a CDR machine is 40-60 Mtrs of fabric per Minute. The fabric is batched on a roll after drying (404). The fabric is folded and packaged (405).

Figure 5:
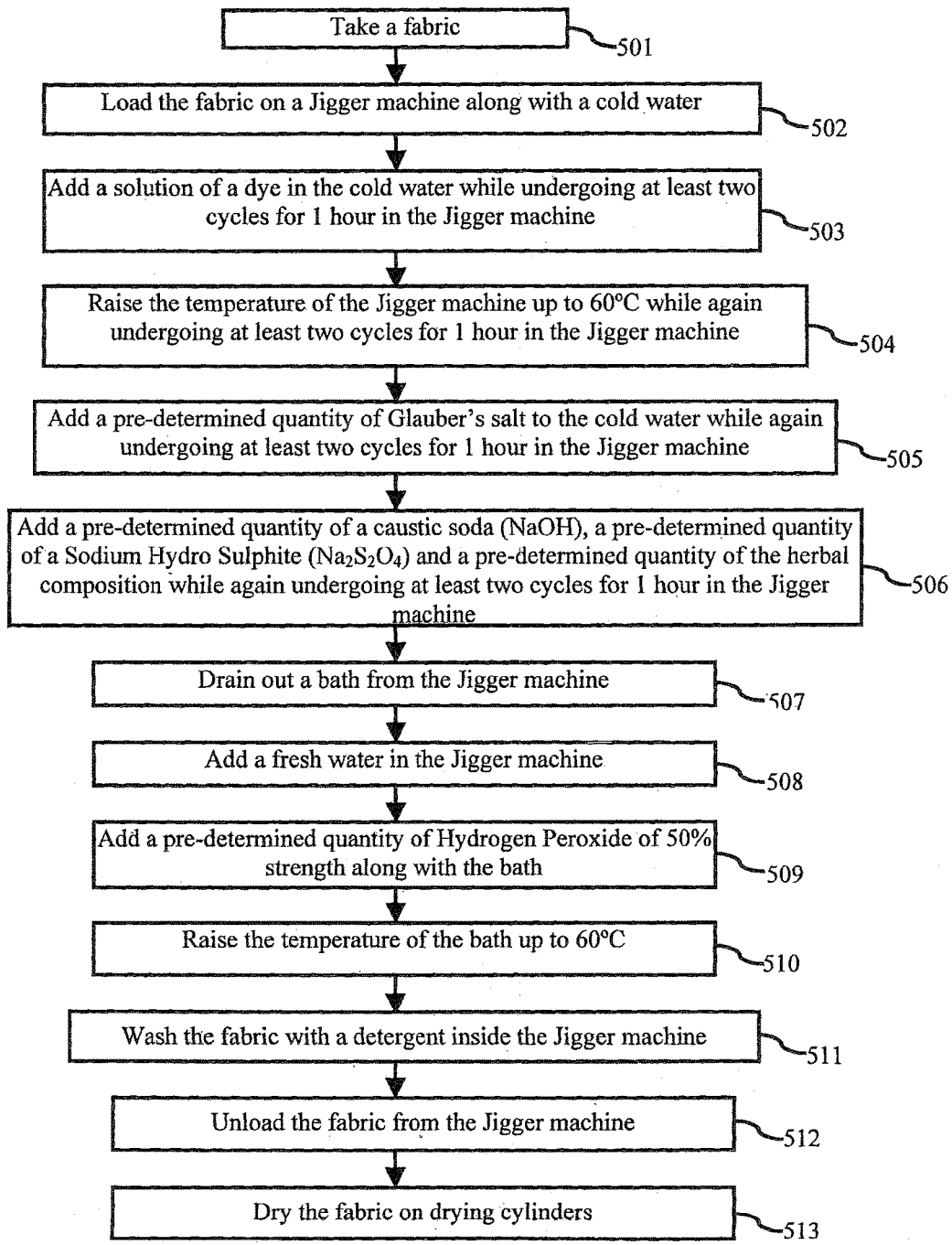
FIG. 5 is a flowchart showing the various steps involved in a method of treating a fabric while dyeing and finishing on a Jigger machine using a dye to render the fabric insect repellent, according to an embodiment herein.

In another embodiment, a method of treating a fabric while dyeing and finishing on a Jigger machine using a dye to render the fabric insect repellent is provided. FIG. 5 is a flowchart showing the various steps involved in the method of treating a fabric while dyeing and finishing on a Jigger machine using a dye to render the fabric insect repellent, according to an embodiment herein. With respect to FIG. 5, a fabric is taken (501). The fabric is loaded on a Jigger machine along with cold water (502). A solution of a dye is added in the cold water while undergoing at least two cycles for 1 hour in the Jigger machine (503). The temperature of the Jigger machine is raised up to 60° C. while again undergoing at least two cycles for 1 hour in the Jigger machine (504). A pre-determined quantity of Glauber's salt is added to the cold water while again undergoing at least two cycles for 1 hour in the Jigger machine (505). The pre-determined quantity of Glauber's salt is 10-20 gpl. A pre-determined quantity of a caustic soda (NaOH), a pre-determined quantity of a Sodium Hydro Sulphite ($Na_2S_2O_4$) and a pre-determined quantity of the herbal composition is added to the Jigger machine while again undergoing at least two cycles for 1 hour in the Jigger machine (506). The pre-determined quantity of the caustic soda (NaOH) is 10 gpl. The pre-determined quantity of the Sodium Hydro Sulphite ($Na_2S_2O_4$) is 10 gpl. The pre-determined quantity of the herbal composition is 4% w/w. The bath is then drained out from the Jigger machine (507). A fresh water is added in the Jigger machine (508). A pre-determined quantity of Hydrogen Peroxide ($H_2O_2$) of 50% strength is added along with the bath in the jigger machine (509). The pre-determined quantity of Hydrogen Peroxide is 0.50 gpl. The temperature of the bath is raised up to 60° C. (510). The fabric is washed with a detergent inside the Jigger machine (511). The fabric is unloaded from the Jigger machine (512) and dried on the drying cylinders (513). The dye is selected from the group consisting of a VAT dye and a Reactive dye.

Figure 6:
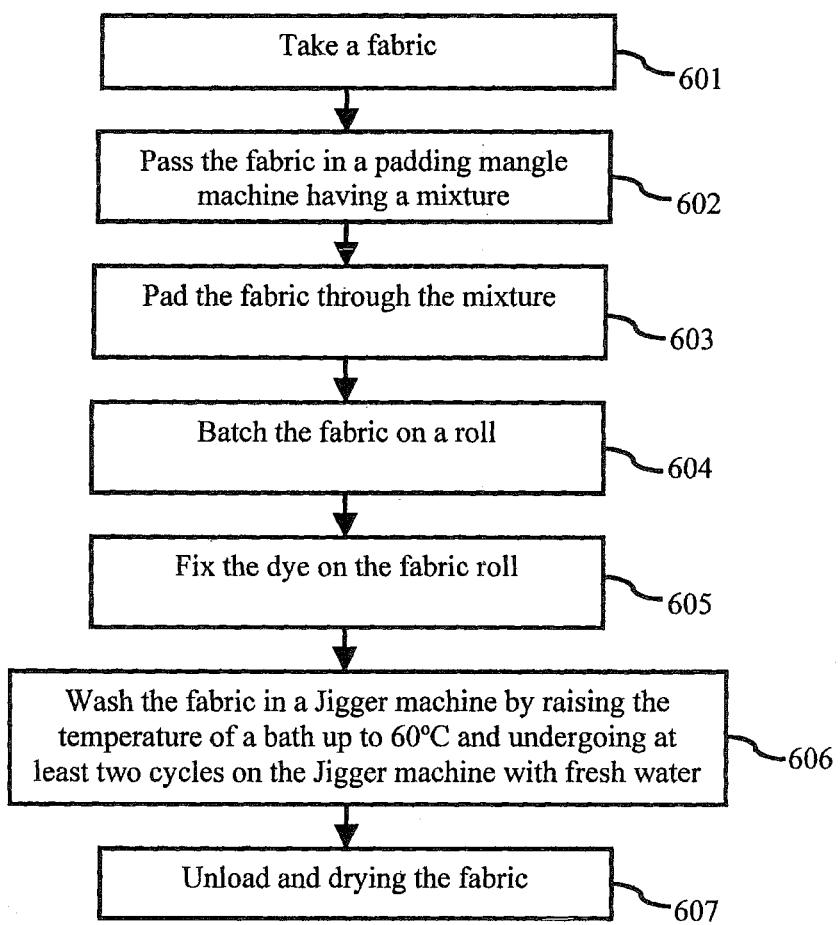
FIG. 6 is a flowchart showing the various steps involved in a method of treating a fabric in a Pad Batch Method of dyeing to render the fabric insect repellent, according to an embodiment herein.

In another embodiment, a method of treating a fabric in a Pad Batch Method of dyeing to render the fabric insect repellent is provided. FIG. 6 is a flowchart showing the various steps involved in the method of treating a fabric in a Pad Batch Method of dyeing to render the fabric insect repellent, according to an embodiment herein. With respect to FIG. 6, a fabric is taken (601). The fabric is passed in a padding mangle machine having a mixture (602). The mixture comprises Sodium Silicate ($Na_2SiO_3$), a dye and an herbal composition. The quantity of the herbal composition is 20-25 gpl. The fabric is padded through the mixture (603). The fabric is batched on a roll (604). A dye is fixed on the fabric roll (605). The fabric is washed in a Jigger machine by raising the temperature of a bath up to 60° C. and undergoing at least two cycles on the Jigger machine with fresh water (606). The fabric is unloaded and dried (607). The herbal composition comprises azadiradione in an amount of 30 to 250 ppm, fraxinellone in an amount of 15 to 125 ppm, nimbin in an amount of 450 to 2400 ppm, salannin in an amount of 110 to 2050 ppm, salannol in an amount of 168 to 3800 ppm, vepinin in an amount of 15 to 125 ppm and vilasinin in an amount of 15 to 125 ppm.

Figure 7:
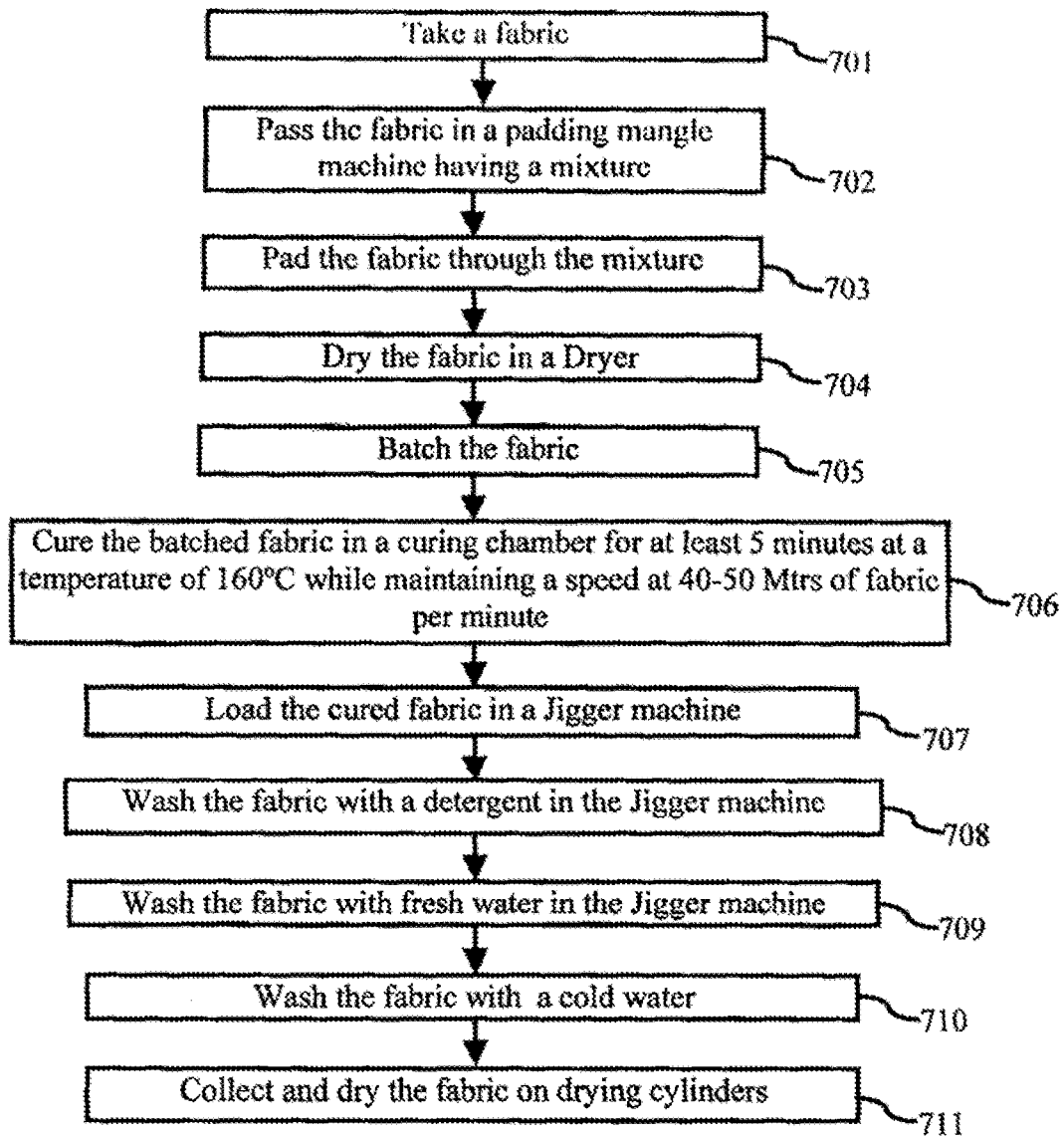
FIG. 7 is a flowchart showing the various steps involved in a method of treating a fabric in a Pad Cure Method of dyeing to render the fabric insect repellent, according to an embodiment herein.

In another embodiment, a method of treating a fabric in a Pad Cure Method of dyeing to render the fabric insect repellent is provided. FIG. 7 is a flowchart showing the various steps involved in the method of treating a fabric in a Pad Cure Method of dyeing to render the fabric insect repellent, according to an embodiment herein. With respect to FIG. 7, a fabric is taken (701). The fabric is passed in a padding mangle machine having a mixture (702). The mixture comprises 5-10 gpl of a Sodium Bicarbonate (NaHCO3) and 20-25 gpl of an herbal composition. The fabric is padded through the mixture (703). The fabric is dried in a Dryer (704). The fabric is batched (705). The batched fabric is cured in a curing chamber for at least 5 minutes at a temperature of 160° C. while maintaining a speed at 40-50 Mtrs of fabric per minute (706). The cured fabric is loaded in a Jigger machine (707). The fabric is washed with a detergent in the Jigger machine while raising the temperature of a bath up to 60° C. and undergoing at least two cycles on the Jigger machine (708). The fabric is washed with fresh water in the Jigger machine while raising the temperature of the bath up to 60° C. and undergoing at least two cycles on the Jigger machine (709). The fabric is washed with cold water undergoing at least two cycles on the Jigger machine (710). The fabric is collected and dried on drying cylinders (711). The herbal composition comprises azadiradione in an amount of 30 to 250 ppm, fraxinellone in an amount of 15 to 125 ppm, nimbin in an amount of 450 to 2400 ppm, salannin in an amount of 110 to 2050 ppm, salannol in an amount of 168 to 3800 ppm, vepinin in an amount of 15 to 125 ppm and vilasinin in an amount of 15 to 125 ppm.

Figure 8:
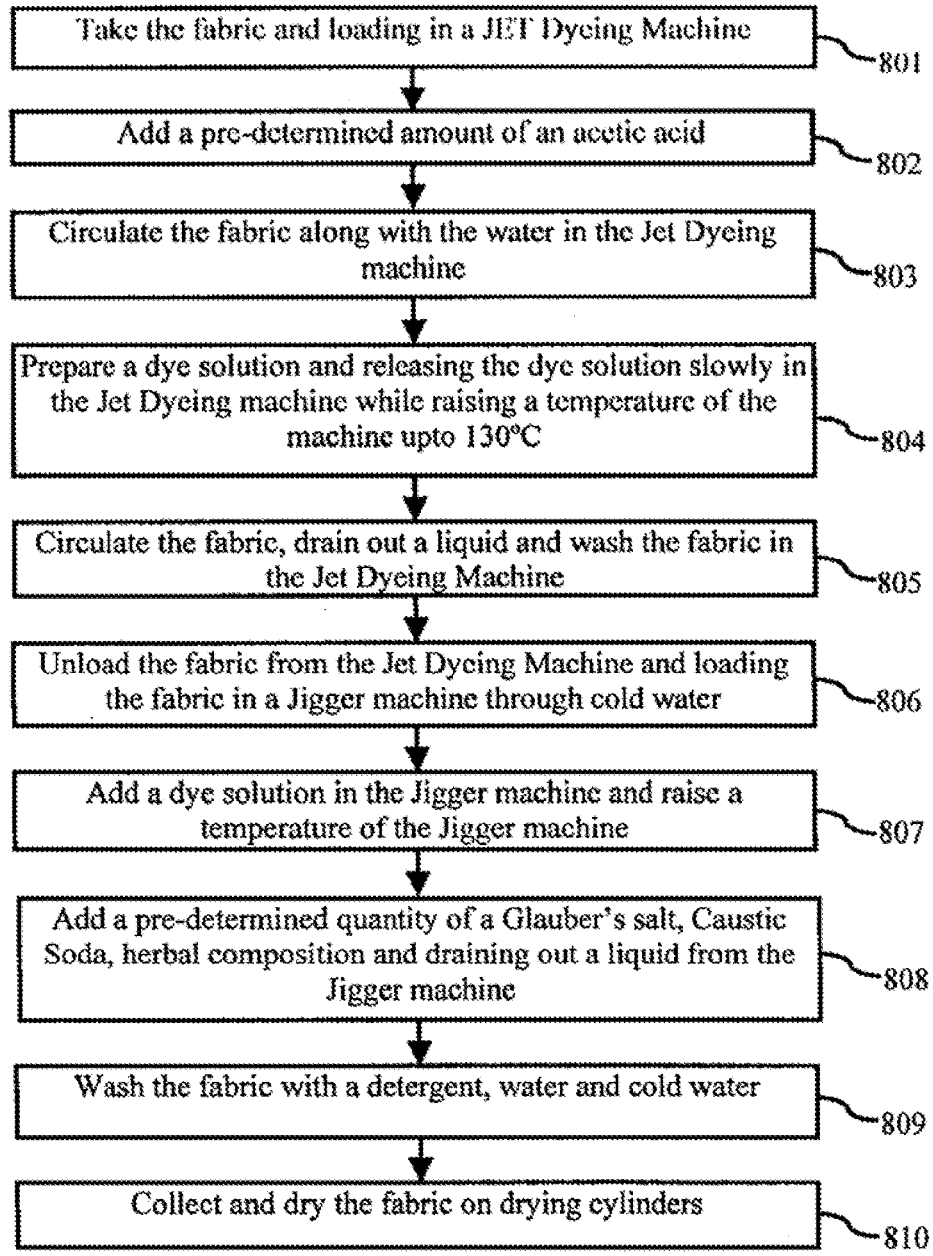
FIG. 8 is a flowchart showing the various steps involved in a method of treating a polyester fabric to render the fabric insect repellent, according to an embodiment herein.

In another embodiment, a method for treating a blended fabric is provided. The method of treating a polyester fabric to render the fabric insect repellent is provided. FIG. 8 is a flowchart showing the various steps involved in the method of treating a polyester fabric to render the fabric insect repellent, according to an embodiment herein. With respect to FIG. 8, the fabric is taken and loaded in a JET Dyeing Machine along with water (801). A pre-determined amount of an acetic acid is added to maintain a pre-determined pH (802). The pre-determined amount of the acetic acid is 0.50 gpl. The pre-determined pH is 4.5 to 5.5. The fabric is circulated along with the water in the Jet Dyeing machine (803). The fabric is circulated for at least 10 minutes at a speed of 80 Mtrs per minute. A dye solution is prepared and released slowly in the Jet Dyeing machine while raising a temperature of the machine upto 130° C. (804).

The fabric is circulated along with the water in the Jet Dyeing machine for a time period of 45-60 minutes. The liquid is drained out of the machine. The fabric is washed in the Jet Dyeing Machine (805).

The fabric is unloaded from the Jet Dyeing Machine. The fabric is loaded in a Jigger machine through cold water (806).

A dye solution is added in the Jigger machine. The temperature of the Jigger machine is raised up to 60° C. while undergoing at least two cycles (807).

The pre-determined quantity of a Glauber's salt (Na2SO4) is added while undergoing at least two turns evenly on the Jigger machine. The pre-determined quantity of the Glauber's salt is 10-20 gpl. A pre-determined quantity of a Caustic Soda (NaOH) and a pre-determined quantity of an herbal composition is added while undergoing at least two cycles on the Jigger machine. The pre-determined quantity of the Caustic Soda (NaOH) is 10 gpl. The pre-determined quantity of the herbal composition is 4% w/w. The liquid is drained out a from the Jigger machine (808).

The fabric is washed with a detergent in the Jigger machine while raising the temperature of a bath up to 60° C. and undergoing at least two cycles on the Jigger machine. The fabric is washed with fresh water in the Jigger machine while raising the temperature of the bath up to 60° C. and undergoing at least two cycles on the Jigger machine. The fabric is washed with cold water while undergoing at least two cycles on the Jigger machine (809).

The fabric is collected and dried on the drying cylinders (810). The herbal composition comprises azadiradione in an amount of 30 to 250 ppm, fraxinellone in an amount of 15 to 125 ppm, nimbin in an amount of 450 to 2400 ppm, salannin in an amount of 110 to 2050 ppm, salannol in an amount of 168 to 3800 ppm, vepinin in an amount of 15 to 125 ppm and vilasinin in an amount of 15 to 125 ppm.

The herbal composition is one of the most effective herbal insect repellants. The herbal composition is based on 'NEEM OIL' extracted from the seeds of 'Neem Tree' (Botanical Name: *Azadirachia Indica*) and is effective in repelling bed bugs (*cimex* species), house dust mites (*Dermatophagoides* species), ticks (*ixodes* species), houseflies (*Musca domestica*), mosquitoes (*Aedes Aegypti*), harvest bugs (*Trombidium* species) and other arthropods. The herbal composition is non-toxic to mammals and is free from Red Listed & Banned items including pesticides. The herbal composition is especially formulated for textile applications and a treatment with the herbal composition imparts the textiles or the textile products an excellent insect repellency which is tumble wash durable too.

The 'Neem Tree' scientifically known as *Azadirachia Indica*, is a big tree commonly found in the tropical & sub-tropical regions of Indian sub-continent. The Neem tree has tremendous medicinal properties and all of the parts of the tree are being widely used in Ayurveda & Unani systems of healing for curing several diseases. The Neem contains wide varieties of bioflavonoids that are well known for repelling insects, fighting against a host of diseases including cancer, diabetes, etc. and purifying the atmosphere on larger perspective. The seeds of Neem Tree are rich in lipid content as well as bitter principles like azadirachtin, azadiradione, fraxinellone, nimbin, salannin, salannol, vepinin, vilasinin, etc. The azadirachtin is one of the most important ingredients of the Neem seed oil extract and is known to have been used as an effective repellent to more than 200 insect species. Simultaneously, it is reported to be non-toxic to humans and other mammals. The present invention provides a Neem seed based herbal composition with unique properties of repelling insects and incorporates the herbal composition in fabrics to render the fabrics insect repellant. The bioflavonoid, especially, azadirachtin is the most active ingredient of the composition in the present invention. The herbal composition with their applications on textiles interferes with the parasite infestations in the human surroundings and creates a protective cover for the humans and their belongings by repelling the undesirable parasites away from them.

The herbal based formulation is reengineered by incorporating and implementing human safe and environment friendly intermediaries and technical processes for making it usable in textile applications. For achieving the desired effects of the treatment. The herbal composition is applied over the textiles of all kinds including cotton, regenerated cellulose (viscose), wool, silk, polyester and blends thereof.

In an embodiment, the active ingredients of the herbal composition comprise azadirachtin, azadiradione, fraxinellone, nimbin, salannin, salannol, vepinin and vilasinin. Azadirachtin is a chemical compound belonging to the limonoid group. The Azadirachtin is a secondary metabolite present in the Neem seeds. The Azadirachtin is a highly oxidized tetranortriterpenoid which boasts a plethora of oxygen functionality, comprising an enol ether, acetal, hemiacetal and tetra-substituted oxirane as well as a variety of carboxylic esters. The chemical features of the chemical Azadirachtin is shown in Table 1.

TABLE 1

The chemical features of Azadirachtin

| | |
|---|---|
| IUPAC Name | dimethyl (2aR,3S,4S,R,S,7aS,8S,10R,10aS,10bR)-10-(acetyloxy)-3,5-dihydroxy-4-[(1S,2S,6S,8S,9R,11S)-2-hydroxy-11-methyl-5,7,10-trioxatetracyclo[6.3.1.02,6.09,11]dodec-3-en-9-yl]-4-methyl-8-{[(2E)-2-methylbut-2-enoyl]oxy}octahydro-1H-furo[3',4':4,4a]naphtho[1,8-bc]furan-5,10a(8H)-dicarboxylate |
| Molecular Formula | $C_{35}H_{44}O_{16}$ |
| Molecular Weight | 720.71426 g/mol |
| Structural Formula | 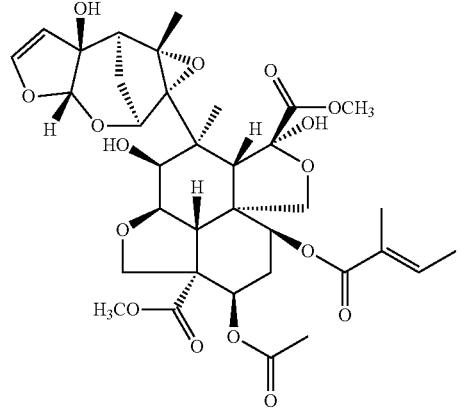<br>Azadirachtin |

Azadirachtin was initially found to be active as a feeding inhibitor towards the desert locust (*Schistocerca gregaria*). The Azadirachtin is now known to affect over 200 species of insect, by acting mainly as an anti-feedant and growth disruptor, and as such it possesses considerable toxicity toward insects. The Azadirachtin fulfills many of the criteria needed for a natural insecticide if it is to replace synthetic compounds. The Azadirachtin is biodegradable as it degrades within 100 hours when exposed to light and water and shows very low toxicity to mammals making it practically non-toxic.

Azadiradione is another triterpenoid present in the Neem seed oil that actually passes through elaborate biosynthesis process pathway for formation of Azadirachtin finally. Azadiradione is a chemical belonging to limonoid group and is found to be highly effective in repelling and eradicating insects. The chemical features of the chemical Azadirachtin is shown in Table 2.

TABLE 2

The chemical features of Azadiradione

| | |
|---|---|
| IUPAC Name | [(8R,10R)-17-(furan-3-yl)-4,4,8,10,13-pentamethyl-3,16-dioxo-6,7,9,11,12,17-hexahydro-5H-cyclopenta[a]phenanthren-7-yl] acetate |
| Molecular Formula | $C_{28}H_{34}O_5$ |
| Molecular Weight | 450.56656 g/mol |
| Structural Formula | Azadiradione 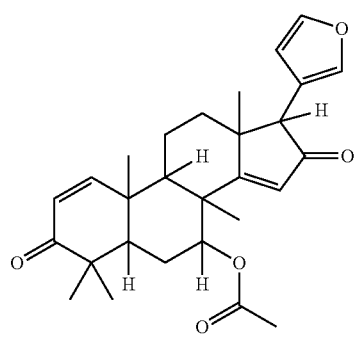 |

Fraxinellone is another bitter principal compound found in the Neem seed oil extract that is formed by the natural degradation of limonoids. Besides the insecticidal properties, Fraxinellone has also been reported to possess neuroprotective and vasorelaxing properties. The chemical features of the chemical Fraxinellone is shown in Table 3.

TABLE 3

The chemical features of Fraxinellone

| | |
|---|---|
| IUPAC Name | (3R,3aR)-3-(furan-3-yl)-3a,7-dimethyl-3,4,5,6-tetrahydro-2-benzofuran-1-one |
| Molecular Formula | $C_{14}H_{16}O_3$ |
| Molecular Weight | 232.27504 g/mol |
| Structural Formula | 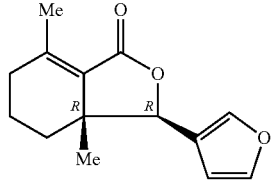 Fraxinellone |

Nimbin is a chemical compound classified as triterpenoid isolated from Neem seed oil. Nimbin is thought to be responsible for much of the biological activities of Neem tree and is reported to have anti-inflammatory, antipyretic, antifungal, antihistamine and antiseptic properties. The chemical features of the chemical Nimbin is shown in Table 4.

TABLE 4

The chemical features of Nimbin

| | |
|---|---|
| IUPAC Name | Methyl (2R,3aR,4aS,5R,5aR,6R,9aR,10S,10aR)-5-(acetyloxy)-2-(furan-3-yl)-10-(2-methoxy-2-oxoethyl)-1,6,9a,10a-tetramethyl-9-oxo-3,3a,4a,5,5a,6,9,9a,10,10a-decahydro-2H-cyclopenta[b]naphtho[2,3-d]furan-6-carboxylate |
| Molecular Formula | $C_{30}H_{36}O_9$ |
| Molecular Weight | 540.60144 g/mol |
| Structural Formula | 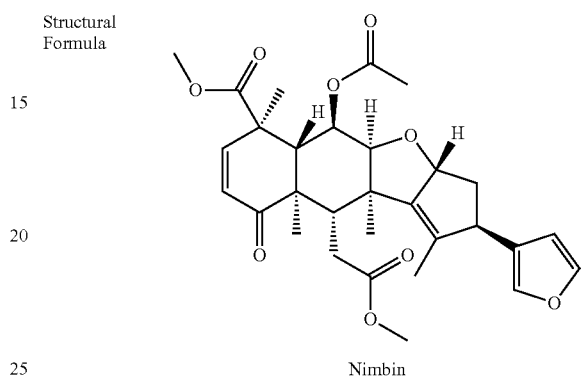 Nimbin |

The salannin, salannol, vepinin and vilasinin form the collective bitter principals of Neem seed oil extract apart from azadirachtin, azadiradione and salannin and do have a major role in biosynthetic transformation of triterpenoids into tetranortriterpenoids like Azadirachtin. The chemical features of the chemical salannin are shown in Table 5.

TABLE 5

The chemical features of Salannin

| | |
|---|---|
| IUPAC Name | 2H,3H-Cyclopenta(d')naphtho(1,8-bc:2,3-b')difuran-6-acetic acid, 3-(acetyloxy)-8-(3-furanyl)-2a,4,5,5a,6,6a,8,9,9a,10a,10b,10c-dodecahydro-2a,5a,6a,7-tetramethyl-5-(((2E)-2-methyl-1-oxo-2-butenyl)oxy)-, methyl-ester, (2aR,3R,5S,5aR,6R,6aR,8R,9aR,10aS,10bR,10cR)- |
| Molecular Formula | $C_{34}H_{46}O_9$ |
| Molecular Weight | 596.70776 g/mol |
| Structural Formula | 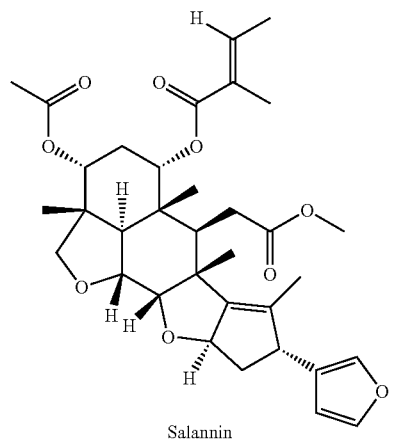 Salannin |

The chemical features of the chemical Salannol is shown in Table 6.

TABLE 6

The chemical features of Salannol

| | |
|---|---|
| IUPAC Name | |
| Molecular Formula | C$_{30}$H$_{36}$O$_9$ |
| Molecular Weight | 540.60144 g/mol |
| Structural Formula | |

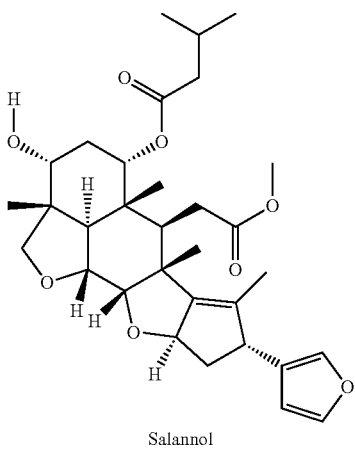

Salannol

The chemical features of the chemical Vepinin is shown in Table 7.

TABLE 7

The chemical features of Vepinin

| | |
|---|---|
| IUPAC Name | 24-Norchola-1,20,22-trien-3-one, 6-acetyloxy)-7,15:21,23-diepoxy-4,4,8-trimethyl-, (5a,6a,7a,13a,15b,17a)-(9CI) |
| Molecular Formula | C$_{28}$H$_{36}$O$_5$ |
| Molecular Weight | 452.58240 g/mol |
| Structural Formula | Vepinin |

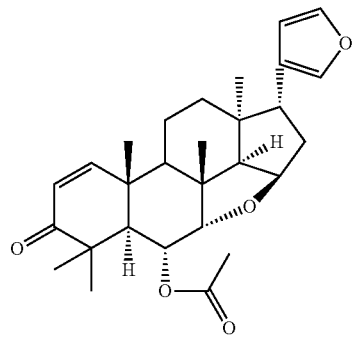

The chemical features of the chemical Vilasinin is shown in Table 8.

TABLE 8

The chemical features of Vilasinin

| | |
|---|---|
| IUPAC Name | (13S,17R)-21,23-Epoxy-4,5α,5',6β-tetrahydro-4β,8-dimethyl-24-norchol-5-eno[6,5,4-bc]furan-14,20,22-triene-1α,3α,7α-triol |
| Molecular Formula | C$_{26}$H$_{36}$O$_5$ |

TABLE 8-continued

The chemical features of Vilasinin

| | |
|---|---|
| Molecular Weight | 428.56104 g/mol |
| Structural Formula | |

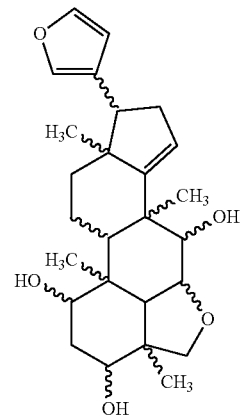

Vilasinin

All the active ingredients of the composition of the present invention belong to the bioflavonoid class of chemicals that occur naturally in the Neem Seed Oil extract. Most important of all ingredients is azadirachtin which was initially found to be active as a feeding inhibitor towards the desert locust (*Schistocerca gregaria*), it is now known to affect over 200 species of insect, by acting mainly as an antifeedant and growth disruptor, and as such it possesses considerable toxicity toward insects. It fulfills many of the criteria needed for a natural insecticide if it is to replace synthetic compounds. Many more compounds, related to azadirachtin, are present in the seeds as well as in the leaves and the bark of the Neem tree which also show strong biological activities among various pest insects. The effects of these preparations on beneficial arthropods are generally considered to be minimal. Some laboratory and field studies have found Neem extracts to be compatible with biological control. Because pure Neem oil contains other insecticidal and fungicidal compounds in addition to azadirachtin. Azadirachtin is generally considered appropriate to be used as a natural pesticide as compared to the synthetic ones which might be hazardous to mammals and create environmental imbalance too.

The Pigment Binder used in the present invention and the treatment process is known as "KCP-1" which is a poly acrylate binder by nature. The pigment binder is used in the treatment process for achieving the enhancement of wash fastness and for stability of the substrate during laundering process. The KCP-1 comprises ethyl acrylate polymer binder, amino silicon emulsion and polyethylene glycol.

The Anti-Thermo Migrating Agent used in the present invention and the treatment process is known as "KCP-2" which is a humectant by nature. The Anti-Thermo Migrating Agent is used in the treatment process to avoid a migration of the product under the present invention from a dorsal to a ventral surface of the substrate especially when subjected to high temperature of 160° C. curing process on stenters. This way the product under the present invention spreads and penetrates into the substrate evenly despite of high temperature on the ventral surface than the dorsal one. The KCP-2 comprises amino silicon emulsion and polyethylene glycol.

The Amino Silicon Emulsion used in the present invention and the treatment process is known as "BOUNCY-R" which is a Permanent Softener by nature. The Amino Silicon Emulsion is used in the treatment process to improve wash fastness and the stability of the substrate during laundering process, as well as to impart softness to the substrate. Chemically, the BOUNCY-R is somewhat water repellent and therefore it also provides support in maintaining longevity of the finish through permanent binding. The bouncy-R comprises amino silicon emulsion.

The VAT dyes are themselves a special class of textile dyes that are used for dyeing of fabric of cotton and other cellulosic types. The VAT dyes have excellent colour fastness to washing and light. The VAT dyes generally give out dull shades after fixation and may be found in various colours like yellow, orange, blue, green, olive green, grey and black. These colours can be used either alone or in combination thereof depending upon the kind and depth of the required shades. All kinds of Vat dyes are used in the present invention.

The Reactive Dyes are themselves a special class of textile dyes that react with cellulosic material and molecules thereof during dye fixation and hence the name. The Reactive Dyes are used for dyeing of fabric of cotton and other cellulosic types. The Reactive Dyes have a good colour fastness to washing however medium colour fastness to light. There can be several types of Reactive Dyes depending upon the reactive groups like vinyl sulfon, cyanuric acid chloride, etc. The reactive dyes give out bright colours after fixation and may be found in various colours such as yellow, orange, blue, t. blue, green, red and black. These colours can be used either alone or in combination thereof depending upon the kind and depth of the required shades. All kinds of reactive dyes can be used in the present invention.

EXPERIMENTAL DATA

The possible effect of azadirachtin and other bioflavonoids including azadiradione, fraxinellone, nimbin, salannin, salannol, vepinin and vilasinin, the active components of the Neem seed oil extract, are inhibiting molting in larvae to pupae and adults of the most of the insects. Apart from delayed lethal action, effects on the pupation, adult emergence, and size of pupae or adults have been also observed. A baseline exposure for 10 or 20 min, ranging from 0.00001 to 0.1 µg/ml, when used, it was found causing about 20 or 22.5 to 83.5 or 97.6% inhibition (inhibition of adult-concentration-probability lines). The compounds are characterized by their inhibition or prevention of formation of adult morphology. The effects on pupae (based on proportion of undeveloped individuals) and adults (based on incomplete development, attachment to puparia, or inability to fly) are dose-dependent.

The development from third larval to adult is completely inhibited by exposure to 0.1 µg/ml of composition for 20 min (97.58%). No adults of insects are obtained at doses of 1.10, 10 and 100 µg/ml. These concentrations cause about 100% mortality of larvae or developed pupae. The results show a reduction in insect's size as a function of azadirachtin exposure. There seems to be a direct relationship between the size of the resulting pupae or adult males and females, since treatment of larvae with 0.00001 to 0.1 µg/ml of azadirachtin causes significant reductions in the pupal weights and dimensions, adult weights, wing dimensions, or interocular distances. The treatments with 0.00001 and 0.001 µg/ml would result in an insignificant increase (0.8-1.6%) in the female wing length/width. The concentrations of 0.001, 0.01 and 0.1 µg/ml also do not significantly affect the wing dimensions of females.

The textile products treated with the composition under our invention have been tested thoroughly by a competent laboratory of international repute and the same have been established to be nontoxic to humans and other mammals. The methodology of this test is based on the perspectives of "INVITRO CYTOTOXICITY TEST" and the test standards followed are namely, ISO-10993-5:2009 (E)—*Biological Evaluation of Medical Devices: Test for Invitro Cytotoxicity* and EN ISO 10993-12:2004 (E)—*Biological Evaluation of Medical Devices; Sample Preparation and Reference Materials*. The above test standards are predetermined to check for the toxicity that any material may be causing to humans and other mammals and the same are internationally accredited and accepted as well.

The test for cytotoxicity is designed to determine the biological response of mammalian cells to the test material/extract of test material. At the end of exposure time, the evaluation of the presence and the extent of cytotoxic effect are assessed. It signifies the Biological Compatibility of the test material and its potential to cause cell damage.

So far the effectiveness of the solution as offered by the composition under our invention is concerned, it has been established to be capable in repelling maximum exo-parasites that may come into contact of the textile products that have been treated with the composition. The tests of the effectiveness of the solution as offered by the composition under the present invention have been conducted by the same competent laboratory of international repute where textile products treated with the composition of the present invention were infested with live bed bug population and after the exposure time it was inferred that the treated substrate (textile product) was capable of repelling the bed bugs as well as disallowing them to feed through the nutritional medium thereby stopping their population to grow further.

The methodology of this test is based on the perspectives of "ANTI-BED BUG TEST" and the test standard followed is ISO 3998-1977 (E); 2002 where the live Bed Bugs are exposed for a short span like 15 minutes to the treated substrate (textile product) that is held through blood membrane, to feed from the substrate. After this exposure time, it is checked and determined as to how many Bed Bugs from the population have escaped the substrate/composition present in it. It is also determined if the Bed Bugs have been forced not to feed on the blood membrane due to the presence of the composition in the substrate. The test findings were suggestive of:

a) the treated substrate was found to be capable of repelling most of the bed bugs away thus suggesting the high effectiveness of the composition under our invention, b) the composition under the invention present in the treated substrate did stop most of the bed bugs from feeding upon the blood membrane thus suggesting the effectiveness of it in creating an unfavorable atmosphere for the parasites to draw nourishment and grow, and c) the bed bug population was seen to be ovulating at higher speed as more number of eggs than normal were found there. This suggested for the effectiveness of the composition under the present invention in the sense that it posed the bed bug population a real threat of extinction forcing them to tend to reproduce more under the natural instinct.

The composition according to the present invention does address the issue of 'Longevity of Effectiveness' more emphatically. As mentioned earlier, effectiveness of currently present solutions to the problem remains under big question for the fact that the same is not found to last for longer time hence allowing the parasites the opportunity to return to the human surroundings once the effectiveness of the solutions gets diminished over a period of time.

The composition according to the present invention has been tested for longevity of its effectiveness by the same competent laboratory of international repute and it has been inferred that the effectiveness is long lasting. The textile products treated with the composition under the present invention were subjected to laundering up to a number of wash cycles and tested for understanding the effectiveness longevity. In fact the substrate was machine washed up to 40 wash cycles and tested for bed bug repellency and it was found to be moderately effective in repelling the bed bug population. This inference suggests that the textile products even though washed up to 40 wash cycles but is capable of moderately repelling the bed bug population. This indicates towards the fact that the composition once applied onto textiles/textile products, binds strongly with the substrate and the treatment may not fade away easily even after 40 number of washes thus defending the human surrounding against the infestation of exo-parasites on long term basis.

The present invention has been an outcome of continuous thought process and research done extensively to provide such a solution to the problem under discussion. The composition under the present invention is found to be the perfect solution in the sense that it has longevity more than other solutions and does not have any adverse effects on human health and surroundings at all. The composition has been designed and prepared with formulation based on herbal extracts of Neem Tree (Botanical Name: *Azadirachta Indica*) seeds by incorporating hi-tech scientific method for making the raw materials usable for the purpose. It is taken care of during the refinement process and preparation of the final product that the natural characteristics of the raw material do not vanish. It is also ensured that the scientific process or any of the additives do not interfere into or disturb the natural essence of the raw materials but keep the same intact in all the applications thereafter.

The composition according to the present invention has been especially designed for applications on textiles/textile products for achieving excellent insect repellency. On the merit of the composition's chemical properties and accuracy & longevity of its effectiveness on exo-parasites mainly insects of different kinds, it has been developed most precisely and exclusively for use into textile applications.

The composition under this invention has been engineered in a way that it can be very well applied onto textiles during normal processing without affecting the nature and composition of the same. Its versatility in terms of application onto textiles is also recommendable for the reason that it can be incorporated into all kinds of processes of all types of textile products for achieving the desired effectiveness that lasts longer too.

The embodiments herein are further described by way of following non-limiting example:

Example 1

Materials Required for the Operation:

the herbal composition developed in the present invention, other textile finishing chemicals for processing, namely, pigment binder, anti-thermo migrating agent, amino silicon emulsion, Glauber's salt, acetic acid, sodium silicate and sodium bicarbonate.

Other materials that are required for carrying out the operation in the present invention includes textile dyes such as VAT, reactive, pigment and disperse.

Machineries Required:

Textile Processing Machineries, namely Singeing Machine, Jigger, Stenter, CPB (Cold Pad Batch) Machine, Jet Dyeing Machine, Soft Flow Dyeing Machine, CDR (Continuous Dyeing Range), VDR (Vertical Drying Range), Mercerizing Machine, Sanforizing Machine.

Utilities involved in textile processing, namely steam, electricity, compressed air, water and gas.

Example 2

Chemistry of Organic Polymer

The Oil is expelled from the Neem Seeds and filtered. Saponification of the filtered Neem Seed Oil is done. To 25 Kgs of filtered Neem Oil, about 60 Liters of water is added and stirred with high speed at room temperature. During stirring only 7 Kgs of Caustic Soda/Potash Liquid (1:1) is added slowly and speedily stirred till 30 minutes and kept overnight afterwards. Next morning, it is added with 15 Kgs of Glauber's Salt (Na2SO4) and stirred and kept for about 4 hours. Once separation occurs, the Saponified Neem Oil Extract floats above the water. It is separated by removing the excess water and is stirred again by adding with 50 Liters of fresh water. Then, around 1 Kg of 70% Sulpuric Acid (H2SO4) is slowly added to it in order to neutralize the free alkali and to bring the pH around 7. Then, 4.1 Kg of Emulsifier (Alcohol Ethoxylate) is now added to this formulation for achieving further good emulsification. At least 10 Kgs of Glauber's Salt (Na2SO4) or Vacuum Salt/Common Salt (NaCl) is added to it for achieving exhaustion during application. This formulation is now replenished with some 15 Liters of fresh water totaling to 100 Kgs of the final yield. This yield is hereafter called "Organic Polymer 4933" and is prepared for commercial applications/sale.

Example 3

Bleached Finishing (White)

The bleached fabrics are subjected to the treatment process. The herbal composition is prepared by mixing all the herbal ingredients in their effective amounts. The herbal ingredients comprise azadiradione, fraxinellone, nimbin, salannin, salannol, vepinin and vilasinin. Table 9 shows the composition of the herbal composition according to the present invention.

TABLE 9

Composition of the herbal composition

| Ingredients | Amount in parts per million (ppm) |
|---|---|
| azadiradione | 30 to 250 ppm |
| fraxinellone | 15 to 125 ppm |
| nimbin | 450 to 2400 ppm |
| salannin | 110 to 2050 ppm |
| salannol | 168 to 3800 ppm |
| vepinin | 15 to 125 ppm |
| vilasinin | 15 to 125 ppm |

Other additives such as the pigment binder, anti-thermo migrating agent, amino silicon emulsion, Glauber's salt and the acetic acid are added in their effective amount as mentioned in table 10.

TABLE 10

Composition with their effective amounts used herein

| Ingredients | Effective Amount |
|---|---|
| Herbal composition of present invention | 20-25 gpl |
| Pigment Binder | 12-15 gpl |
| Anti-Thermo Migrating Agent | 2-5 gpl |
| Amino Silicon Emulsion | 5 gpl |
| Glauber's Salt | 5 gpl |
| Acetic Acid | 0.5 gpl (to maintain pH of 5.5 to 6.5) |

The fabric is then padded, dried and cured simultaneously at 160° C. with 22 to 25 meters/min of speed followed by sanforization and other finishes, if necessary.

Example 4

Bleached Finishing on Stenter

The present invention is used on the bleached fabrics on Stenter machine also. A Stenter machine is used for evenly stretching or stentering the fabrics. The bleached fabric of any count and construction is taken along with the blend composition. The fabric is padded on the Stenter using the solution having the composition shown in Table 11.

TABLE 11

Composition with their effective amounts used herein

| Ingredients | Effective Amount |
|---|---|
| Herbal composition of present invention | 22-25 gpl |
| Pigment Binder | 12-15 gpl |
| Anti-Thermo Migrating Agent | 2-5 gpl |
| Amino Silicon Emulsion | 5 gpl |
| Glauber's Salt | 5 gpl |
| Acetic Acid | 0.5 gpl (to maintain pH of 5.5 to 6.5) |

The herbal composition has a composition as mentioned in table 9 above. The fabric is then dried on the Stenter maintaining a temperature from 110° C. in the first compartment followed by 160° C. in the next two compartments of the Stenter. The speed of the fabric in the Stenter is maintained at 20-25 Mtrs of fabric per minute. The batching of the fabric is done on the roll after drying is over. The batching is a continuous process and is done simultaneously with padding and drying processes. The bleached and the treated fabric are then sent to folding department and quality check followed by packaging.

Dye Finishing

Example 5

VAT Dyeing & Finishing on Jigger

The ready for dyeing (RFD) 100% cotton fabric is taken. The cotton fabric is of any count and construction. The fabric is then loaded on a Jigger through cold water. A pre-dispersed m/f VAT dyestuff is added to the cold water keeping the m:1 ratio of 1:4 in two installments. The time consumed to complete two cycles of VAT dyeing is approximately 1 hour. The temperature is then raised to 60° C. and the fabric is worked for another two turns inside the jigger. Then, pre-dissolved 10-20 gpl of Glauber's salt ($Na_2SO_4$) is added to the bath depending upon the required depth of the shade for enhancing further exhaustion. Two turns are given evenly and the time consumed is approximately 1 hour. Further, the caustic soda (NaOH) of 10 gpl is added on solid basis and 10 gpl of Sodium Hydro Sulphite ($Na_2S_2O_4$) is also added to the bath in two equal installments to convert the VAT dyestuff into Leuco VAT Dyestuff with 4% w/w of the herbal composition of the present invention. The composition is as mentioned in the Table 9 above. The fabric is worked till two turns and the time taken is approximately 1 hour. The bath is drained and the fresh water is taken into the jigger. An equivalent quantity of 0.50 gpl of Hydrogen Peroxide ($H_2O_2$) of 50% strength is added to the bath. The temperature is raised to 60 C to convert the water soluble Leuco VAT Dye(s) into parent VAT Dye(s). Two turns consuming about 1 hour is are given to the fabric during this process and the liquor is drained out. The fresh water is again taken into the jigger and added with 2 gpl and equivalent quantity of detergent and temperature is raised to 60° C. Two turns of about 30 minutes each are given to the fabric and the liquor is drained out. Again the fresh water is taken in the Jigger and the temperature is raised to 60° C. and the fabric is again given tow turns of 30 minutes each in the hot water in order to remove the traces of the detergent by rinsing. The water is finally drained out and the fabric is given cold water wash in two turns of 30 minutes each. During the second turn, the fabric is unloaded to batch outside the jigger. The fabric is dried on frying cylinders and subjected to further processing on Stenter for required finishes.

Example 6

VAT Dyeing on Stenter (Alternative Route for Finishing of VAT Dyed Fabrics on Stenter)

The VAT dyed 100% cotton fabric of any count and construction is taken. The fabric is padded on the Stenter using the herbal composition of the present invention as mentioned in table 9 along with the plurality of additives mentioned in table 12 with the mentioned amounts:

TABLE 12

Amount of ingredients used

| Herbal composition of present invention | 22-25 gpl |
|---|---|
| Pigment Binder | 12-15 gpl |
| Anti-Thermo Migrating Agent | 2-5 gpl |
| Amino Silicon Emulsion | 5 gpl |
| Glauber's Salt | 5 gpl |
| Acetic Acid | 0.5 gpl (to maintain pH of 5.5 to 6.5) |

The fabric is dried on the Stenter maintaining the temperature from 110° C. in the first compartment followed by 160° C. in the next two compartments of the Stenter with a speed maintenance at 20-25 Mtrs of fabric per minute.

Example 7

Reactive Dyeing on Jigger

The ready for dyeing (RFD) 100% cotton fabric of any count and construction is taken and loaded on the jigger machine through cold water. A pre-dispersed reactive dyestuff is then added to the cold water keeping m:l ration of 1:4 in two installments. The time consumed to complete the two cycles of reactive dyeing is approximately 1 hour. Then, the temperature is raised to 60° C. and the fabric is worked for another two turns inside the Jigger. A pre-dissolved 10-20 gpl of Glauber's salt is added to the bath depending upon the required depth of the shade for enhancing further exhaustion. Then two turns is given evenly and the time of consuming is approximately 1 hour. Then, the caustic soda of 10 gpl and equivalent quantity is added on solid basis to the bath in two equal installments to fix the dyestuff along with 4% w/w of the herbal composition of the present invention as mentioned in Table 9 above. The fabric is worked upon for two cycles for which the time taken is approximately 1 hour. The liquor is then drained out.

The fresh water is taken into the Jigger and added with 2 gpl equivalent quantity of a detergent raising the temperature to 60° C. The fabric is worked for two turns of about 30 minutes each and the liquor is drained out. Unfixed and hydrolyzed Reactive Dyestuff is removed by the detergent. Again fresh water is taken in the Jigger raising the temperature to 60° C. The fabric is again given two turns of 30 minutes each in the hot water in order to remove the traces of detergent by rinsing. The water is finally drained out and fabric is given cold water wash in two turns of 30 minutes each. During the second turn, the fabric is unloaded to batch outside the Jigger.

The fabric is dried on drying cylinders and subjected to further processing on Stenter for required finishes.

Example 8

Alternative Route for Finishing the Reactive Dyed Fabrics on Stenter Machine

Reactive Dyed 100% Cotton Fabric of any count and construction is taken and padded on the Stenter machine using the solution having composition as mentioned in table 13.

TABLE 13

Amount of the ingredients used herein

| Ingredients | Amount |
| --- | --- |
| Herbal composition | 22-25 gpl |
| Pigment Binder | 12-15 gpl |
| Anti-Thermo Migrating Agent | 2-5 gpl |
| Amino Silicon Emulsion | 5 gpl |
| Glauber's Salt | 5 gpl |
| Acetic Acid | 0.5 gpl |
| | (To maintain the pH of 5.5 to 6.5) |

The fabric is then dried on the Stenter machine maintaining the temperature at 110° C. in the first compartment followed by 160° C. in the next two compartments of Stenter while maintaining the speed at 20 to 25 Mtrs of fabric per Minute. The batching is done on the roll after the drying process is over. The batching is a continuous process and done simultaneously with padding and drying processes. The finished and treated reactive dyed fabric is now sent to folding department for cut looking and packing.

Example 9

Reactive Dyeing by Pad Batch Method

The Ready for Dyeing (RFD) 100% cotton fabric of any count and construction is taken. The fabric is passed through a Padding Mangle containing an instant mixture of 200 liters of 100 gpl of Sodium Silicate ($Na_2SiO_3$) Liquid with 600 liters of reactive dyestuff solution containing 20-25 gpl the herbal composition of the present invention as mentioned in table 9. The fabric is padded through this mixture and batched. The batched fabric roll is then covered with a plastic sheet to avoid drying and is kept continuously rotating at a speed of 4 rpm for about 10-12 hours for an even reactive dye fixation.

Now the fabric is loaded on to the Jigger for washing. The fresh water is taken into the Jigger and added with 2 gpl equivalent quantity of a detergent while raising the temperature to 60° C. The fabric is given at least two turns of about 30 minutes each and the liquor is drained out. The fresh water is again taken into the Jigger and the temperature is raised to 60° C. and the fabric is again given two turns of 30 minutes each in the hot water in order to remove the traces of detergent by rinsing. The water is finally drained out and fabric is given cold water wash in two turns of 30 minutes each. The fabric is unloaded to batch outside the Jigger while during the second turn. The fabric goes through the following five compartments while undergoing the washing:

Soaper's $1^{st}$ Compartment: Cold water Wash
Soaper's $2^{nd}$ Compartment: Hot water soaping with 4 gpl of Detergent.
Soaper's $3^{rd}$ Compartment: Hot water wash
Soaper's $4^{th}$ Compartment: Cold water wash
Soaper's $5^{th}$ Compartment: Additional Cold water wash The fabric is then dried on the drying cylinders and subjected to further processing on the Stenter for required finishes.

Example 10

Reactive Dyeing by Pad Cure Method

The Ready for Dyeing (RFD) 100% cotton fabric of any count and construction is taken. The fabric is passed through a Padding Mangle containing reactive dyestuff solution which comprises 5-10 gpl of Sodium Bicarbonate ($NaHCO_3$) and 20-25 gpl of the herbal composition of the present invention as mentioned in table 9 above. The fabric is padded through this mixture, dried on Float Dryer and batched. The fabric batch is taken to curing chamber for hot air curing at temperature of 160° C. for 5 minutes by maintaining the speed at 40-50 Mtrs of fabric per minute.

Now the fabric is loaded on to the Jigger for washing. The fresh water is taken into the Jigger and added with 2 gpl equivalent quantity of a detergent while raising the temperature to 60° C. The fabric is given at least two turns of about 30 minutes each and the liquor is drained out. The fresh water is again taken into the Jigger and the temperature is raised to 60° C. and the fabric is again given two turns of 30 minutes each in the hot water in order to remove the traces of detergent by rinsing. The water is finally drained out and fabric is given cold water wash in two turns of 30 minutes each. The fabric is unloaded to batch outside the Jigger while during the second turn. The fabric goes through the following five compartments while undergoing the washing:

Soaper's $1^{st}$ Compartment: Cold water Wash
Soaper's $2^{nd}$ Compartment: Hot water soaping with 4 gpl of Detergent.
Soaper's $3^{rd}$ Compartment: Hot water wash
Soaper's $4^{th}$ Compartment: Cold water wash
Soaper's $5^{th}$ Compartment: Additional Cold water wash The fabric is then dried on the drying cylinders and subjected to further processing on the Stenter for required finishes.

Example 11

Dyeing & Finishing on CDR or Stenter Using Pigment Ink of any Class of Dyes

RFD (Ready for Dyeing) Fabric of any count, construction and blend composition are taken. The fabric is padded on CDR or Stenter using the solution containing the composition shown in Table 14.

TABLE 14

Amount if ingredients used herein

| Ingredients | Amount |
| --- | --- |
| Pigment Ink | up to 5 gpl |
| Herbal composition | 22-25 gpl |
| Pigment Binder | 12-15 gpl |
| Anti-Thermo Migrating Agent | 2-5 gpl |
| Amino Silicon Emulsion | 5 gpl |
| Glauber's Salt | 5 gpl |
| Acetic Acid | 0.5 gpl |
| | (To maintain the pH of 5.5 to 6.5) |

The fabric is dried on the CDR or Stenter maintaining the temperature from 110° C. till 160° C. with speed at 20 to 25 Mtrs of fabric per Minute on Stenter and 40 to 60 Mtrs of fabric per Minute on CDR. The batching is done on the roll after the drying process is over. The batching is a continuous process and done simultaneously with padding and drying processes. The dyed, treated and finished fabric is now sent to folding department for cut looking and packing.

Example 12

Alternative Route for Finishing of Pigment Ink Dyed Fabrics on Stenter

The pigment ink dyed fabric of any count, construction and blend composition are taken and the fabric is padded on Stenter using the solution having the composition mentioned in table 15.

TABLE 15

Amount of the ingredients used herein

| Ingredients | Amount |
| --- | --- |
| Herbal composition | 22-25 gpl |
| Pigment Binder | 12-15 gpl |
| Anti-Thermo Migrating Agent | 2-5 gpl |
| Amino Silicon Emulsion | 5 gpl |
| Glauber's Salt | 5 gpl |
| Acetic Acid | 0.5 gpl |
| | (To maintain the pH of 5.5 to 6.5) |

The fabric is then dried on the Stenter machine maintaining the temperature at 110° C. in the first compartment followed by 160° C. in the next two compartments of Stenter maintaining the speed at 20 to 25 Mtrs of fabric per Minute. The batching is done on the roll after the drying process is over. The batching is a continuous process and done simultaneously with padding and drying processes. The finished and treated pigment ink dyed fabric is now sent to folding department for cut looking and packing.

Example 13

Two-Step Method for Cotton/Polyester Blended Fabric Dyeing

Polyester Component Dyeing:

The RFD (Ready for Dyeing) Fabric of any count, construction and blend composition are taken. The RFD fabric is loaded on to JET Dyeing Machine along with water. Then, acetic acid with an amount of 0.50 gpl after dilution is added to the loaded fabric to maintain a pH of the solution at 4.5 to 5.5. The water and the fabric are circulated for 10 minutes at a speed of 80 Mtrs per Minute in order to ensure uniform pH. The Dyes solution is prepared by dispersing the dye in cold water outside the tank. The solution is prepared by taking proportionate quantity of the dyes so that it goes up to a maximum of 6% w/w of Polyester contents keeping m:l ratio of 1:10 depending upon the required depth of shades. The Disperse Dyes Solution is then released slowly into the Jet Dyeing Machine while circulating the water and the fabric as earlier. The temperature is then raised to 130° C. and the process is carried out 45-60 minutes depending upon the required depth of shades. The liquor is drained out of the Jet Dyeing Machine after the process is over. This is followed by a cold water wash till 30 minutes. Afterwards, the water is drained out and fabric is unloaded into trolley.

Cotton Component Dyeing:

Firstly, the fabric is loaded on the Jigger Machine through cold water. The pre-dispersed Reactive Dyestuff is then added to the cold water keeping m:l ratio of 1:4 in two installments. The time consumed to complete the two cycles of the reactive dyeing is approximately 1 hour. The quantity of reactive dyestuff taken depends upon the depth of required shades and the percentage of cotton content.

The temperature is to be raised to 60° C. and the fabric is worked for another two turns inside the Jigger machine. A pre-dissolved Glauber's salt ($Na_2SO_4$) with a quantity of 10-20 gpl depending upon the required depth of the shade is added to the bath for enhancing further exhaustion. The fabric is given at least two turns evenly. The time consumed is approximately 1 hour.

A Caustic Soda Liquid (NaOH) with an equivalent quantity of 10 gpl is added to the bath on solid basis in two equal installments to fix the Dyestuff along with 4% w/w of the herbal composition of the present invention as mentioned in table 9 above. The fabric is worked for two more turns. The time taken is approximately 1 hour. The liquor is then drained out of the Jigger.

The fresh water is taken into the Jigger machine and added with 2 gpl equivalent quantity of a detergent and the temperature is raised to 60° C. The two turns of about 30 minutes each are given to the fabric and the liquor is drained out. The unfixed and hydrolyzed reactive dyestuff is removed by the detergent. The fresh water is again taken into the Jigger and the temperature is raised to 60° C. The fabric is again given at least two turns of 30 minutes each in the hot water to remove the traces of detergent by rinsing. The water is finally drained out and fabric is given cold water wash in two turns of 30 minutes each. During the second turn, the fabric is unloaded to batch outside the Jigger.

The fabric is dried on the drying cylinders and subjected to further processing on Stenter for required finishes.

A treatment that is based on herbal formulations and eventually is human safe and environment friendly too. It has been found and established that the composition according to the present invention is non-toxic to humans and other mammals while it does not pose any threat/hazards to the environment too. The treatment is handled at ease and is incorporated into the regular process flow of textiles/textile products without impacting or affecting in terms of cost, time and efforts. The composition according to the present invention has been designed in such a way that it can be used to create the desired properties in the substrates right by adding the same into the usual process route with all ease and without any hassles.

The herbal composition is authenticated and established to be safe for humans and other mammals. The herbal composition does not create any ecological imbalance for the reason that the formulation is based on natural products and does not contain any such hazardous substances that create any environmental imbalance ever. The herbal composition has better longevity of the effectiveness. The effectiveness of the herbal formulation is established and authenticated by conduction due experiments and show that the herbal composition is effective on a fabric till the 40 times washes. The herbal composition does not leave any appearance, odor or visibility on the fabric. The herbal composition rather intermingles with the textile's basic structure and imparts every bit of it with the unique property of insect repellency.

The treated fabrics with the composition according to the present invention are non-toxic to mammals and are free from Red Listed & Banned items including the pesticides. The treatment process according to the present invention imparts the textiles or textile products with excellent exoparasite repellency. The treatment process is safe for humans and the environment. The ingredients used for making the herbal composition are eco-friendly and are easily available which in turn make the treatment process economic. The treatment process is cost effective and easy to use. The treatment process according to the present invention does not create any ecological imbalance because of the herbal formulation. The herbal formulation is made up of natural products and do not contain any hazardous substances that can create any environmental imbalance ever. The treatment process is applicable for a wide range of textiles that makes it a most desirous solution for repelling insects and pests of all kinds. The treatment process of the present invention has long effectiveness even after the textile product has been washed for 40 tumble cycles. The treatment process does not show any appearance, odor or visibility on the textile maintaining their design and color finish and imparts insect repellency.

Although the embodiments herein are described with various specific embodiments, it will be obvious for a person skilled in the art to practice the invention with modifications. However, all such modifications are deemed to be within the scope of the claims.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the claims.

We claim:

1. A composition for treating a fabric to make the fabric insect repellent, comprises:
   a herbal composition, wherein the herbal composition comprises azadira-dione, fraxinellone, nimbin, salannin, salannol, vepinin and vilasinin;
   wherein the azadiradione is present in an amount of 30 to 250 ppm;
   wherein the fraxinellone is present in an amount of 15 to 125 ppm;
   wherein the nimbin is present in an amount of 450 to 2400 ppm;
   wherein the salannin is present in an amount of 110 to 2050 ppm;
   wherein the salannol is present in an amount of 168 to 3800 ppm;
   wherein the vepinin is present in an amount of 15 to 125 ppm; and
   wherein the vilasinin is present in an amount of 15 to 125 ppm
   a pigment binder, wherein the pigment binder is poly acrylate binder;
   an anti-thermo migrating agent, wherein the anti-thermo migrating agent is a humectant;
   an amino silicon emulsion, wherein the amino silicon emulsion is a permanent softener;
   a Glauber's salt; and
   an acetic acid.

2. The composition as claimed in claim 1,
   wherein the pigment binder is present in an amount of 12-15 gpl;
   wherein the anti-thermo migrating agent is present in an amount of 2-5 gpl;
   wherein the amino silicon emulsion is present in an amount of 5 gpl;
   wherein the Glauber's salt is present in an amount of 5 gpl; and
   wherein the acetic acid is present in an amount of 0.5 gpl.

3. The composition as claimed in claim 1, wherein:
   the composition inhibits a third larval stage of insects by 97.58%.

4. A method of treating a fabric to make the fabric insect repellent, comprising the steps of:
   adding a herbal composition along with a plurality of additives in a fabric process at a predetermined temperature and at a pre-determined pH,
      wherein the herbal composition comprises azadiradione, fraxinellone, nimbin, salannin, salannol, vepinin and vilasinin;
      wherein the azadiradione is present in an amount of 30 to 250 ppm;
      wherein the fraxinellone is present in an amount of 15 to 125 ppm;
      wherein the nimbin is present in an amount of 450 to 2400 ppm;
      wherein the salannin is present in an amount of 110 to 2050 ppm;
      wherein the salannol is present in an amount of 168 to 3800 ppm;
      wherein the vepinin is present in an amount of 15 to 125 ppm; and
      wherein the vilasinin is present in an amount of 15 to 125 ppm;
   wherein the plurality of additives include a pigment binder, an anti-thermo migrating agent, an amino silicon emulsion, a Glauber's salt and an acetic acid,
      wherein the pigment binder is present in an amount of 12-15 gpl;
      wherein the anti-thermo migrating agent is present in an amount of 2-5 gpl;
      wherein the amino silicon emulsion is present in an amount of 5 gpl;

wherein the Glauber's salt is present in an amount of 5 gpl; and wherein the acetic acid is present in an amount of 0.5 gpl;

wherein the fabric process is a process selected from the group consisting of a sanforization process, a bleach finishing process, a dyed finishing process, and a two step dyeing method for cotton or polyester blended fabric, wherein the dyed finishing process further comprises a dyeing on jigger using a Vat dye, dyeing on jigger using a reactive dye, dyeing by a pad batch method using reactive dyes, dyeing by pad cure method using reactive dyes, continuous dyeing on a Continuous Dyeing Range Machine (CDR) or a Stenter machine with a pigment ink of any class of dyes;

wherein the predetermined temperature is in a range of 60° C.-160° C.; and wherein the predetermined pH is in a range of 5.5-6.5.

5. The method as claimed in claim 4, wherein:
the herbal composition is added in an amount of 20-25 gpl.

6. The method as claimed in claim 4, wherein:
the fabric becomes repellent to a plurality of insects after the treatment, wherein the plurality of insects are bed bugs of *Cimex* species, house dust mites of *Dermatophagoides* species, ticks of *Ixodes* species, houseflies or *Musca Domestica*, mosquitoes or *Aedes Aegypti* and harvest bugs of *Trombidium* species.

7. The method as claimed in claim 4, wherein:
the fabric is selected from the group consisting of a cotton fabric, a regenerated viscose cellulose fabric, a wool fabric, a silk fabric, a polyester fabric and blends thereof.

8. The method as claimed in claim 4, wherein:
the fabric is insect repellent up to 40 times of washes.

9. The method of treating a bleached fabric to render the bleached fabric insect repellent according to claim 4, comprising the steps of:

preparing a herbal composition, wherein the herbal composition is prepared by adding a predetermined amount of azadiradione, a predetermined amount of fraxinellone, a predetermined amount of nimbin, a predetermined amount of salannin, a predetermined amount of salannol, a predetermined amount of vepinin and a predetermined amount of vilasinin, wherein the predetermined amount of azadiradione added is 30 to 250 ppm, the predetermined amount of fraxinellone added is 15 to 125 ppm, the predetermined amount of nimbin added is 450 to 2400 ppm, the predetermined amount of salannin added is 110 to 2050 ppm, the predetermined amount of salannol added is 168 to 3800 ppm, the predetermined amount of vepinin added is 15 to 125 ppm and wherein the predetermined amount of vilasinin added is 15 to 125 ppm;

taking the herbal composition in an amount of 20-25 gpl in a treatment machine;

adding a predetermined amount of plurality of additives to the treatment machine, wherein the plurality of additives are a pigment binder, an anti-thermo migrating agent, an amino silicon emulsion, a Glauber's salt and an acetic acid, and wherein the predetermined amount of the pigment binder is 12-15 gpl, the predetermined amount of the anti-thermo migrating agent is 2-5 gpl, the predetermined amount of the amino silicon emulsion is 5 gpl, the predetermined amount of the Glauber's salt is 5 gpl, and the predetermined amount of the acetic acid is 0.5 gpl;

padding, drying and curing the fabric simultaneously at 160° C. at a speed of 22 to 25 meters/min; and sanforizing the fabric.

10. The method of treating a fabric on a Stenter machine to render the fabric insect repellent according to claim 4, comprising the steps of:

taking a fabric of any count and construction along with a blend composition;

padding the fabric on a Stenter machine using a solution of a herbal composition, wherein the herbal composition comprises an azadiradione in an amount of 30 to 250 ppm, a fraxinellone in an amount of 15 to 125 ppm, a nimbin in an amount of 450 to 2400 ppm, a salannin in amount of 110 to 2050 ppm, a salannol in an amount of 168 to 3800 ppm, a vepinin in amount of 15 to 125 ppm and a vilasinin in an amount of 15 to 125 ppm, and wherein the herbal composition is used in an amount of 22-25 gpl;

adding a plurality of additives in the Stenter machine, wherein the plurality of additives includes a pigment binder in an amount of 12-15 gpl, a antithermo migrating agent in an amount of 2-5 gpl, a amino silicon emulsion in an amount of 5 gpl, a Glauber's salt in an amount of 5 gpl, and an acetic acid in an amount of 0.5 gpl;

drying the fabric on the Stenter machine while maintaining a temperature from 110° C. in a first compartment followed by 160° C. in next two compartments of the Stenter machine at a speed of 20-25 Mtrs of fabric per minute in the Stenter machine;

batching the fabric on a roll after the drying; and folding and packaging the fabric.

11. The method as claimed in claim 10, wherein:
the fabric is selected from the group consisting of a bleached fabric, a VAT dyed fabric, a reactive dyed fabrics, a pigment ink dyed fabric and a combination thereof.

12. The method of treating a fabric while dyeing and finishing on a Continuous Dyeing Range (CDR) machine or on a Stenter machine using a pigment ink of any class of dyes to render the fabric insect repellent according to claim 4, comprising the steps of:

taking a fabric of any count and construction along with a blend composition;

padding the fabric on a machine using a solution of a herbal composition, solution of plurality of additives and a solution of a pigment ink, wherein the herbal composition comprises an azadiradione in an amount of 30 to 250 ppm, a fraxinellone in an amount of 15 to 125 ppm, a nimbin in an amount of 450 to 2400 ppm, a salannin in an amount of 110 to 2050 ppm, a salannol in an amount of 168 to 3800 ppm, a vepinin in amount of 15 to 125 ppm and a vilasinin in an amount of 15 to 125 ppm, and wherein the herbal composition is used in an amount of 22-25 gpl, wherein the plurality of additives includes a pigment binder in an amount of 12-15 gpl, an anti-thermo migrating agent in an amount of 2-5 gpl, an amino silicon emulsion in an amount of 5 gpl, a Glauber's salt in an amount of 5 gpl and an acetic acid in an amount of 0.5 gpl, and wherein the solution of a pigment ink is used in an amount of upto 5 gpl, and wherein the machine is selected from the group consisting of a CDR machine and a Stenter machine;

drying the fabric on the machine while maintaining a temperature from 110° C.-160° C. at a speed, wherein the speed in a Stenter machine is at 20-25 Mtrs of fabric per minute, wherein the speed in a CDR machine is 40-60 Mtrs of fabric per minute;
batching the fabric on a roll after the drying; and
folding and packaging the fabric.

13. The method of treating a fabric while dyeing and finishing on a Jigger machine using a dye to render the fabric insect repellent according to claim 4, comprising the steps of:
taking a fabric;
loading the fabric on a Jigger machine along with cold water;
adding a solution of a dye in the cold water while undergoing at least two cycles for 1 hour in the Jigger machine;
raising the temperature of the Jigger machine up to 60° C. while again undergoing at least two cycles for 1 hour in the Jigger machine;
adding a predetermined quantity of Glauber's salt to the cold water while again undergoing at least two cycles for 1 hour in the Jigger machine, wherein the predetermined quantity of Glauber's salt is 10-20 gpl;
adding a predetermined quantity of a caustic soda (NaOH), a predetermined quantity of a Sodium Hydro Sulphite ($Na_2S_2O_4$) and a pre-determined quantity of the herbal composition while again undergoing at least two cycles for 1 hour in the Jigger machine, wherein the pre-determined quantity of the caustic soda (NaOH) is 10 gpl, wherein the predetermined quantity of the Sodium Hydro Sulphite ($Na_2S_2O_4$) is 10 gpl and wherein the herbal composition comprises an azadiradione in an amount of 30 to 250 ppm, a fraxinellone in an amount of 15 to 125 ppm, a nimbin in an amount of 450 to 2400 ppm, a salannin in amount of 110 to 2050 ppm, a salannol in an amount of 168 to 3800 ppm, a vepinin in amount of 15 to 125 ppm and a vilasinin in an amount of 15 to 125 ppm, wherein the predetermined quantity of the herbal composition is 4% w/w;
draining out a bath from the Jigger machine;
adding fresh water in the Jigger machine;
adding a pre-determined quantity of Hydrogen Peroxide (H2O2) of 50% strength along with the bath in the Jigger machine, wherein the pre-determined quantity of Hydrogen Peroxide is 0.50 gpl;
raising the temperature of the bath up to 60° C.;
washing the fabric with a detergent inside the Jigger machine;
unloading the fabric from the Jigger machine; and
drying the fabric on drying cylinders.

14. The method as claimed in claim 13, wherein:
the dye is selected from the group consisting of a VAT dye and a reactive dye.

15. The method of treating a fabric in a Pad Batch Method of dyeing to render the fabric insect repellent according to claim 4, comprising the steps of:
taking a fabric;
passing the fabric in a padding mangle machine having a mixture, wherein the mixture comprises Sodium Silicate (Na2SiO3), a dye and a herbal composition, wherein the herbal composition comprises an azadiradione in an amount of 30 to 250 ppm, a fraxinellone in an amount of 15 to 125 ppm, a nimbin in an amount of 450 to 2400 ppm, a salannin in amount of 110 to 2050 ppm, a salannol in an amount of 168 to 3800 ppm, a vepinin in amount of 15 to 125 ppm and a vilasinin in an amount of 15 to 125 ppm, wherein the quantity of the herbal composition is 20-25 gpl;
padding the fabric through the mixture;
batching the fabric on a roll;
fixing the dye on the fabric roll;
washing the fabric in a Jigger machine by raising the temperature of a bath up to 60° C. and undergoing at least two cycles on the Jigger machine with fresh water; and
unloading and drying the fabric.

16. The method of treating a fabric in a Pad Cure Method of dyeing to render the fabric insect repellent according to claim 4, comprising the steps of:
taking a fabric;
passing the fabric in a padding mangle machine having a mixture, wherein the mixture comprises 5-10 gpl of a Sodium Bicarbonate ($NaHCO_3$) and 20-25 gpl of a herbal composition, wherein the herbal composition comprises an azadiradione in an amount of 30 to 250 ppm, a fraxinellone in an amount of 15 to 125 ppm, a nimbin in an amount of 450 to 2400 ppm, a salannin in amount of 110 to 2050 ppm, a salannol in an amount of 168 to 3800 ppm, a vepinin in amount of 15 to 125 ppm and a vilasinin in an amount of 15 to 125 ppm;
padding the fabric through the mixture;
drying the fabric in a Dryer;
batching the fabric;
curing the batched fabric in a curing chamber for at least 5 minutes at a temperature of 160° C. while maintaining a speed at 40-50 Mtrs of fabric per minute;
loading the cured fabric in a Jigger machine;
washing the fabric with a detergent in the Jigger machine while raising the temperature of a bath up to 60° C. and undergoing at least two cycles on the Jigger machine;
washing the fabric with fresh water in the Jigger machine while raising the temperature of the bath up to 60° C. and undergoing at least two cycles on the Jigger machine;
washing the fabric with a cold water undergoing at least two cycles on the Jigger machine; and
collecting and drying the fabric on drying cylinders.

17. A method of treating a polyester fabric to render the fabric insect repellent, comprising the steps of:
taking the fabric;
loading the fabric in a JET Dyeing Machine along with water;
adding a pre-determined amount of an acetic acid to maintain a predetermined pH, wherein the pre-determined amount of the acetic acid is 0.50 gpl, wherein the pre-determined pH is 4.5 to 5.5;
circulating the fabric along with the water in the Jet Dyeing machine for at least 10 minutes at a speed of 80 Mtrs per minute;
preparing a dye solution;
releasing the dye solution slowly in the Jet Dyeing machine;
raising a temperature of the machine upto 130° C.;
circulating the fabric along with the water in the Jet Dyeing machine for a time period of 45-60 minutes;
draining out a liquid;
washing the fabric in the Jet Dyeing Machine;
unloading the fabric from the Jet Dyeing Machine;
loading the fabric in a Jigger machine through cold water;
adding a dye solution in the Jigger machine;
raising the temperature of the Jigger machine up to 60° C. while undergoing at least two cycles; adding a predetermined quantity of a Glauber's salt (Na2SO4) while undergoing at least two turns evenly on the Jigger machine, wherein the predetermined quantity of the Glauber's salt is 10-20 gpl;

adding a predetermined quantity of a Caustic Soda (NaOH) and a predetermined quantity of a herbal composition while undergoing at least two cycles on the Jigger machine, wherein the pre-determined quantity of the Caustic Soda (NaOH) is 10 gpl, wherein the herbal composition comprises an azadiradione in an amount of 30 to 250 ppm, a fraxinellone in an amount of 15 to 125 ppm, a nimbin in an amount of 450 to 2400 ppm, a salannin in amount of 110 to 2050 ppm, a salannol in an amount of 168 to 3800 ppm, a vepinin in amount of 15 to 125 ppm and a vHasinin in an amount of 15 to 125 ppm, wherein the predetermined quantity of the herbal composition is 4% w/w;

draining out a liquid from the Jigger machine;

washing the fabric with a detergent in the Jigger machine while raising the temperature of a bath up to 60° C. and undergoing at least two cycles on the Jigger machine;

washing the fabric with fresh water in the Jigger machine while raising the temperature of the bath up to 60° C. and undergoing at least two cycles on the Jigger machine;

washing the fabric with cold water while undergoing at least two cycles on the Jigger machine; and collecting and drying the fabric on drying cylinders.

* * * * *